(12) United States Patent
Schulz

(10) Patent No.: US 11,517,454 B2
(45) Date of Patent: Dec. 6, 2022

(54) HAND PROSTHESIS BASE BODY

(71) Applicant: Stefan Schulz, Karlsruhe (DE)

(72) Inventor: Stefan Schulz, Karlsruhe (DE)

( * ) Notice: Subject to any disclaimer, the term of this patent is extended or adjusted under 35 U.S.C. 154(b) by 215 days.

(21) Appl. No.: 16/477,294

(22) PCT Filed: Jan. 14, 2018

(86) PCT No.: PCT/EP2018/025008
§ 371 (c)(1),
(2) Date: Jul. 11, 2019

(87) PCT Pub. No.: WO2018/130428
PCT Pub. Date: Jul. 19, 2018

(65) Prior Publication Data
US 2019/0374353 A1  Dec. 12, 2019

(30) Foreign Application Priority Data

Jan. 14, 2017  (DE) .................. 10 2017 000 229

(51) Int. Cl.
*A61F 2/58* (2006.01)
*A61F 2/70* (2006.01)
*A61F 2/68* (2006.01)

(52) U.S. Cl.
CPC .............. *A61F 2/586* (2013.01); *A61F 2/70* (2013.01); *A61F 2002/587* (2013.01); *A61F 2002/6836* (2013.01)

(58) Field of Classification Search
CPC .. A61F 2/586; A61F 2/583; A61F 2/70; A61F 2002/587; A61F 2002/6836
See application file for complete search history.

(56) References Cited

U.S. PATENT DOCUMENTS

| | | | | |
|---|---|---|---|---|
| 2,582,234 A | * | 1/1952 | Conzelman, Jr. ....... | A61F 2/583 623/61 |
| 2,669,727 A | * | 2/1954 | Opuszenski .............. | A61F 2/58 623/64 |
| 2,701,370 A | * | 2/1955 | Alderson ................ | A61F 2/583 623/24 |
| 2,847,678 A | * | 8/1958 | Opuszenski .............. | A61F 2/58 623/64 |

(Continued)

FOREIGN PATENT DOCUMENTS

| | | |
|---|---|---|
| DE | 10 2013 001 809 A1 | 8/2014 |
| DE | 10 2014 001 393 A1 | 8/2015 |

(Continued)

OTHER PUBLICATIONS

International Search Report Corresponding to PCT/EP2018/025008 dated May 15, 2018.

(Continued)

*Primary Examiner* — Yashita Sharma
*Assistant Examiner* — Melissa A Hoban
(74) *Attorney, Agent, or Firm* — Finch & Maloney, PLLC; Michael Bujold; Jay Franklin

(57) ABSTRACT

A hand prosthesis base body having an outer side, a motor, and a first rotatable shaft which is connected with an output shaft of the motor. The first rotatable shaft has a coupling element for a detachably coupling at least one finger element to the rotatable shaft.

8 Claims, 25 Drawing Sheets

(56) References Cited

U.S. PATENT DOCUMENTS

| | | | | |
|---|---|---|---|---|
| 3,822,418 | A | * | 7/1974 | Yakobson ............... A61F 2/583 623/25 |
| 4,094,016 | A | * | 6/1978 | Eroyan .................. A61F 2/583 623/24 |
| 5,437,490 | A | * | 8/1995 | Mimura .................... B25J 9/102 294/106 |
| 5,523,662 | A | * | 6/1996 | Goldenberg ............... B25J 9/06 318/568.11 |
| 8,491,666 | B2 | | 7/2013 | Schulz |
| 9,974,667 | B1 | * | 5/2018 | Cazenave ............... A61F 2/586 |
| 2008/0066574 | A1 | * | 3/2008 | Murata ..................... A61F 2/70 74/826 |
| 2013/0041476 | A1 | | 2/2013 | Schulz |
| 2013/0046395 | A1 | * | 2/2013 | McLeary ............... A61F 2/583 623/64 |
| 2014/0107805 | A1 | * | 4/2014 | Varley ................. B25J 15/0009 623/24 |
| 2017/0049583 | A1 | * | 2/2017 | Belter ..................... A61F 2/583 |
| 2018/0110631 | A1 | * | 4/2018 | Cazenave ................ A61F 2/70 |

FOREIGN PATENT DOCUMENTS

| | | |
|---|---|---|
| DE | 10 2014 007 743 A1 | 12/2015 |
| WO | 2010/051798 A1 | 5/2010 |

OTHER PUBLICATIONS

Written Opinion Corresponding to PCT/EP2018/025008 dated May 15, 2018.

* cited by examiner

HAND PROSTHESIS BASE BODY

This application is a National Stage completion of PCT/EP2018/025008 filed Jan. 14, 2018, which claims priority from German patent application serial no. 10 2017 000 229 filed Jan. 14, 2017.

FIELD OF THE INVENTION

The present invention concerns a hand prosthesis base body and a hand prosthesis.

BACKGROUND OF THE INVENTION

Hand prosthesis's are generally used to replace hands at patients. Such hand prosthesis's are supposed to imitate on one hand the look of natural hands but, also on the other side, to enable the patient to perform manual work at least in a way as if the natural hand is still available.

SUMMARY OF THE INVENTION

The task of the present invention is to provide a hand prosthesis base body which is advanced in the state of the art, in particular for instance to provide a hand prosthesis base body and/or hand prosthesis which allows the adaptation of a hand prosthesis for different requirements.

The task is solved through a hand prosthesis base body and/or hand prosthesis according to the independent claim (s). Preferred embodiments can be found in the dependent claims.

In particular, the task is solved through a hand prosthesis base body, comprising an outer side, a motor, and a first rotatable shaft which is functionally connected with the output shaft of a motor, whereby the first rotatable shaft has a coupling element for releasably coupling at least one finger element to the first rotatable shaft.

Thus, it has been recognized that through a releasable connection of a finger element with a first rotatable shaft of a hand prosthesis base body, a hand prosthesis can be provided, comprising a hand prosthesis base body and a finger element. This hand prosthesis can, through the coupling of finger elements which might be matched with the present task, be matched with a plurality of tasks so that they can be mastered.

Based on this background, a finger element, in the following, is understood not only as an element which at least simulates rudimentarily the human finger, it is also generally understood as an element which, compared to the hand prosthesis base body, can be flexibly positioned. In particular, a finger element is to be understood as an element which can move, by a motor which is positioned in the hand prosthesis base body, in reference to the hand prosthesis base body, and in particular can be rotated. The motor for instance, can hereby be positioned in the finger element or in the hand prosthesis base body. The motor can be activated through an energy source, such as a battery or an accumulator, which is positioned in the finger element, or in the hand prosthesis base body, or outside of both. Such a finger element can, for instance, be positioned next to a finger element which is anatomically correct or has a similar look, also a tool such as a knife, hook, etc.

The finger elements to be attached (finger or tools) can also be designed through different mechanics as actively flexible, for instance through a respective coupling with the base body/center hand. The coupling can be realized via gearing, pull cords, springs, or rod links.

It is possible that such a finger element can comprise one or several fingers. The finger element can itself be stiff or flexible. For instance, the finger element can have several joints, such as rotatable joints. The finger element itself can be moved by actuators which can be, for instance, positioned within or outside of the finger element.

The coupling element can be designed as one piece with the rotatable shaft, for instance where the coupling element is positioned in an area of the shaft at which the finger element can be connected with the first rotatable shaft.

Also, the coupling element can be an additional element which, for instance, through interaction with the finger element, allows a detachable connection of the finger element with the first rotatable shaft.

The output shaft of the motor can be directly connected with the first rotatable shaft or functionally connected through several torque transferable elements with the output shaft of the motor, such as a spring, etc.

Hereby, the motor can be an electric motor, such as a servo motor, but also a mechanical motor, such as a spring, etc.

Preferably, the coupling element is designed to move and hold the finger element. Thus, the finger element can be connected by itself through the coupling element with the hand prosthesis base body. This makes the connection of the inner element easier at the hand prosthesis base body. In particular, the finger element can be moved, pivotably around a pivot axis which corresponds with the axis of rotation of the coupling element, relative to the hand prosthesis base body.

Preferably, the rotational axis of the first rotatable shaft is perpendicular to the main axis of the hand prosthesis base body, the first rotatable shaft can be used at the same time as a mounting bracket and as the drive for the finger element. Thus, the hand prosthesis can be simply designed.

Preferably, the coupling element is positioned at the distal end of the hand prosthesis base body. Thus, the combination of the hand prosthesis base body and the finger element can provide an impression which corresponds with the natural human hand.

Also, the first coupling element or an additional coupling element, such as a second coupling element, in a position at the side of the hand prosthesis base body. Thus, the finger element or an additional finger element can be, in accordance with the position of the thumb, positioned on a natural human hand. Preferably, a second rotatable shaft is positioned in the second coupling element.

Preferably, a rotational axis of the second coupling element is parallel to the rotational axis of the first coupling element. Thus, the second finger element can be moved relative to the first finger element and therefore, a tweezer grip can be executed.

The coupling element, such as for instance the first coupling element and/or the second coupling element, can have a non-circular cross-section, to enable an interlocking of the finger element with the coupling element. Thus, the finger element can be even more easily connected with the hand prosthesis base body. In particular the coupling element can have a non-circular receptacle, such as for instance an oblate, square, pentagonal, polygonal, or star shaped receptacle and/or a receptacle with grooves or edges, through which a shaft with a non-circular cross-section or a shaft with an end with a non-circular cross-section can be connected.

Also, the coupling element can also be designed as a shaft with a non-circular cross-section, and the finger element can have a receptacle with a non-circular cross-section which can be interlocked with the coupling element.

Also, the connection between the coupling element and the finger element can be achieved through a friction-locking connection, like with a screw, which detachably connects the finger element and the coupling element from the outside, by itself or in addition to the friction-locking connection. Hereby, the coupling element can also be connected through a magnetic connection, in addition to the friction-locking and/or power-locking connection.

Especially preferred, the coupling element can be detached without tools from the finger element and/or be connected without tools to the finger element.

Detachable from the outside means in this application, that the finger element can be detached from the coupling element, without opening and/or disassembly of the hand prosthesis base body.

Also, a coupling element, such as a third coupling element can be arranged in addition to or instead of the first and/or the second coupling element at the distal end of the hand prosthesis base body. Through the positioning of several coupling elements, several finger elements can be connected with the hand prosthesis base body to achieve an even greater similarity to a natural hand and also a larger number of grip variations.

Preferably, a third shaft which is connected with a third coupling element has a rotational axis which is parallel to the rotational axis of the first rotatable shaft. Through the parallelism of the two rotational axis, the finger elements attached thereto can be moved in parallel planes. Thus, the use of the hand prosthesis becomes even more natural.

Also, a hand prosthesis is taught here with at least a hand prosthesis base body with at least one of the above mentioned characteristics.

Also, a hand prosthesis can be comprised of a hand prosthesis base body and at least one finger element. The hand prosthesis base body and/or the finger element can hereby have an actuating mechanism which, when actuated, enables the release of the finger element from the hand prosthesis base body, wherein the actuating mechanism is designed such that it can be actuated from the outside.

Such an actuator mechanism can comprise an externally actuatable screw which is connected to the finger element and which presses on the hand prosthesis base body for coupling the finger element with the hand prosthesis base body. Also, the actuator mechanism can comprise a bayonet lock, and a magnetic lock, and or a spring-loaded pin, which is connected to the finger element or the hand prosthesis base body and which presses into a matching recess of the hand prosthesis base body or the finger element.

BRIEF DESCRIPTION OF THE DRAWINGS

In addition, the invention is explained with exemplary embodiments with reference to the drawings.

These show.

DETAILED DESCRIPTION OF THE PREFERRED EMBODIMENTS

Figures 1, 2:
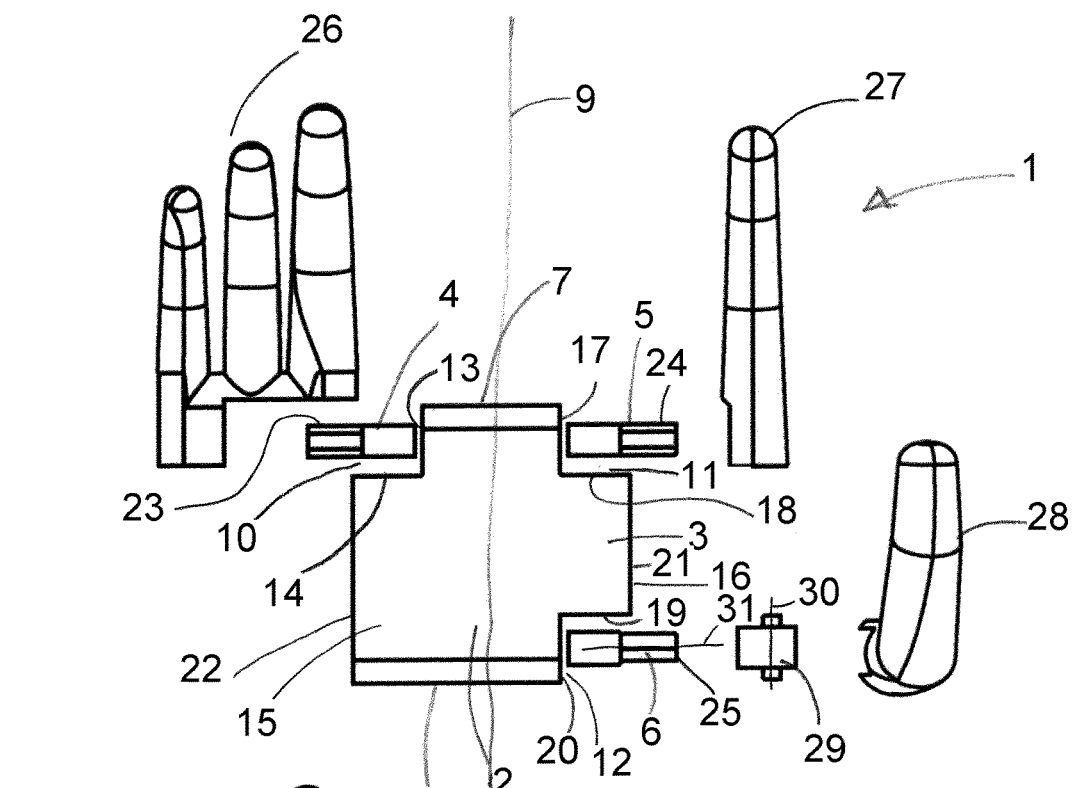
FIG. 1 a hand prosthesis in an exploded view.
FIG. 2 the hand prosthesis as in FIG. 1 in another grip function.

FIG. 1 shows a hand prosthesis 1 in an exploded view. The hand prosthesis 1 comprises a hand prosthesis base body 2.

The hand prosthesis base body 2 comprises of a main element 3, from which a first coupling element 4, a second coupling element 5, and a third coupling element 6 stick out. In this case, the main element 3 has a distal side 7, which faces away from the patient, in particular the arm of the patient, and has a proximal side 8 which faces the patient, in particular the patient's arm. The main axis 9 of the main element 3 can be defined as extending from the distal side 7 to the proximal side 8.

Hereby, the main element 3 can itself be rigid. For instance, the main element 3 can comprise a metal shell, which in particular can be opened. The main element 3 can have one or more recesses, for example three recesses, such as a first recess 10, a second recess 11, and a third recess 12, in which the coupling elements 4, 5, 6 are positioned. Preferably, a coupling element 4, 5, 6 can be positioned in each recess 10, 11, 12. It is also conceivable to position several coupling elements 4, 5, 6 in a recess 10, 11, 12.

The first recess 10 is limited by a first side 13 of the main element 3, wherein the first side 13 extends parallel to the main axis 9, and is bounded by a second side 14 of the main element 3, wherein the second side 14 extends perpendicular to the main axis 9. In other embodiments, the recesses 10, 11, 12 can be limited only from one side of the main element 3, or by more than two sides of the main element 3. Also, the other embodiments of the sides of the main element 3 which limit the recesses 10, 11, 12 can have other orientations. Thus, the sides can for instance be arranged so as to slope in reference to the main axis 9.

In FIG. 1, the first side 13 is perpendicular positioned to the second side 14. The coupling element 4 extends itself through an opening in the first side 13 into the inner part of the main element 3.

The second recess 11 is also positioned at the distal side 7 of the main element 3. The second recess 11 is delimited by a third side 17 of the main element 3, on the one hand, and by a fourth side 18 of the main element 3, on the other hand, at two sides. The third side 17 of the main element 3 is parallel to the main axis 9 of the main element 3. The fourth side 18 runs parallel to the main axis 9 of the main element 3. The third side 17 is perpendicular to the fourth side 18. The third side 17 has at least an opening through which the coupling element 5 extend into the inner part of the main element 3. The third side 17 runs parallel to the first side 13. The third side 17 is connected to the first side 13 by the distal side 7.

The third recess 12 is positioned at the proximal side 8 of the main element 3. The third recess 12 is bounded by a fifth side 19 and a sixth side 20. Hereby, the fifth side 19 is perpendicular to the main axis 9 of the main element 3 and perpendicular to the sixth side 20. This sixth side 20 has hereby an opening through which the third coupling element 6 extends into the inner part of the main element 3.

The sixth side 20 adjoins the proximal side 8 of the main element 3. The first side 13, the second side 14, the third side 17, the fourth side 18, the fifth side 19, the sixth side 20, a right side 21, a left side 22, the proximal side 8, and the distal side 7 adjoin with an upper side 15 and a bottom side 16 of the main element 3. Hereby, the upper side 15 and the bottom side 16 can extend parallel.

Also, a curved upper side 15 and/or a curved bottom side 16 are also possible, which will not run in parallel. Also, the upper side 15, as well as the bottom side 16, as well as the lateral sides 13, 14, 17, 18, 19, 20, 21, 22, 8, 7 can have openings, can be curved and/or can have several, for instance planar surfaces.

Each of the coupling elements 4, 5, 6 is positioned in the recesses 10, 11, 12. The coupling elements 4, 5, 6 each have a mounting area 23, 24, 25. The mounting area 23, 24, 25 is suitable to link a finger element 26, 27, 28 with the coupling element 4, 5, 6. The mounting area 23, 24, 25 has a non-circular cross-section in order to attach, for example, the finger element 26, 27, 28 in a form-fitting manner with the mounting area 23, 24, 25. Hereby, the finger element 26, 27, 28 can have a recess with the same or similar cross-section so that the coupling element 4, 5, 6 can be partially accommodated at least with its mounting area 23, 24, 25 in the finger element 26, 27, 28. The connection between the finger element 26, 27, 28 and the coupling element 4, 5, 6 can be secured via a securing means, such as, for example, an externally accessible screw. It is also possible that a joint 29, such as a pivot joint is positioned between the coupling element 4, 5, 6 and the finger element 26, 27, 28. The joint 29 can hereby have a rotational axis 30 which is perpendicular to the main axis 31 of the coupling element 6.

FIG. 2 shows the hand prosthesis 1 as in FIG. 1 comprising the hand prosthesis base body 2 and the finger elements 26, 27, 28.

The finger element 26 comprises three finger partial elements 32, 33, 34 which correspond with to the natural fingers of the lithe finger, the ring finger, the middle finger. The finger partial elements 32, 33, 34 are more or less parallel and extend approximately perpendicular to a rotational axis 36 of coupling element 4. The finger elements 32, 33, 34 are connected proximal with each other and have a common mounting area 35 to which the coupling element 4 can be attached to.

The coupling element 6 can be connected at its mounting area 25 either detachably or firmly with the joint 29. The joint 29 has two pins 38, 39 which extend coaxially, which are positioned at the side of the joint 29 and which define the rotational axis 30 of the finger element 28. The finger element 28, which can be a replica of the human thumb, has two limbs 41, 42. The limbs 41, 42 are positioned parallel to each other and can rotatably accommodate the pins 38, 39. A finger section 43, which adjoins the area of the limbs 41, 42, has about an angle of 60° in reference to the main axis of the limbs.

The finger element 27 is a replica of the human index finger. It has a mounting area 44 and a partial finger element 45 which extends perpendicular to the rotational axis 46 of the coupling element 5.

Figure 3:
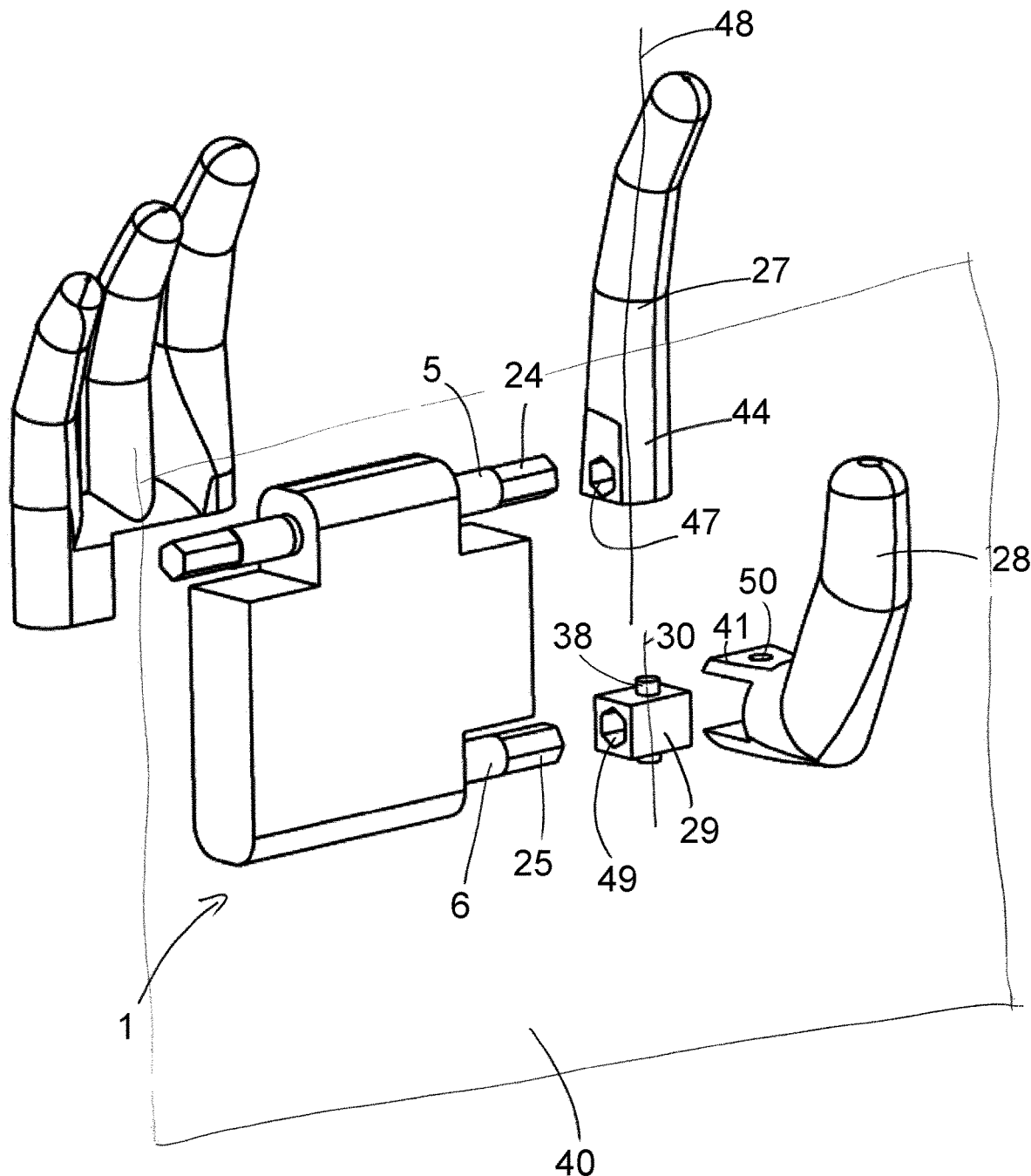
FIG. 3 the hand prosthesis as in FIG. 1 from another perspective.

FIG. 3 shows the hand prosthesis 1 in a spatial presentation. Herein, an opening 47 can be seen which is positioned in the mounting area 44 of the finger element 27. The opening 47 corresponds in form and size with the cross-section, approximately the form and size of the cross section of the mounting area 24 of the coupling element 5. The opening 47 extends more or less perpendicular to the main axis 48 of the finger element 27.

An opening 49 can also be seen which is positioned at the joint 29. The size and the form of the cross section of the opening 49 correspond with the size and form of the cross section of the mounting area 25 of the coupling element 6. The opening 49 extends perpendicular to the rotational axis 30 of the joint 29.

An opening 50 can also be seen which is positioned at the limb 41 of the finger element 28 which serves for the rotatable accommodation of the pin 38. Hereby, the pin 30 has a circular cross section. The opening 50 has cross section of size and form which matches the cross section of the pin 38.

Figure 4:
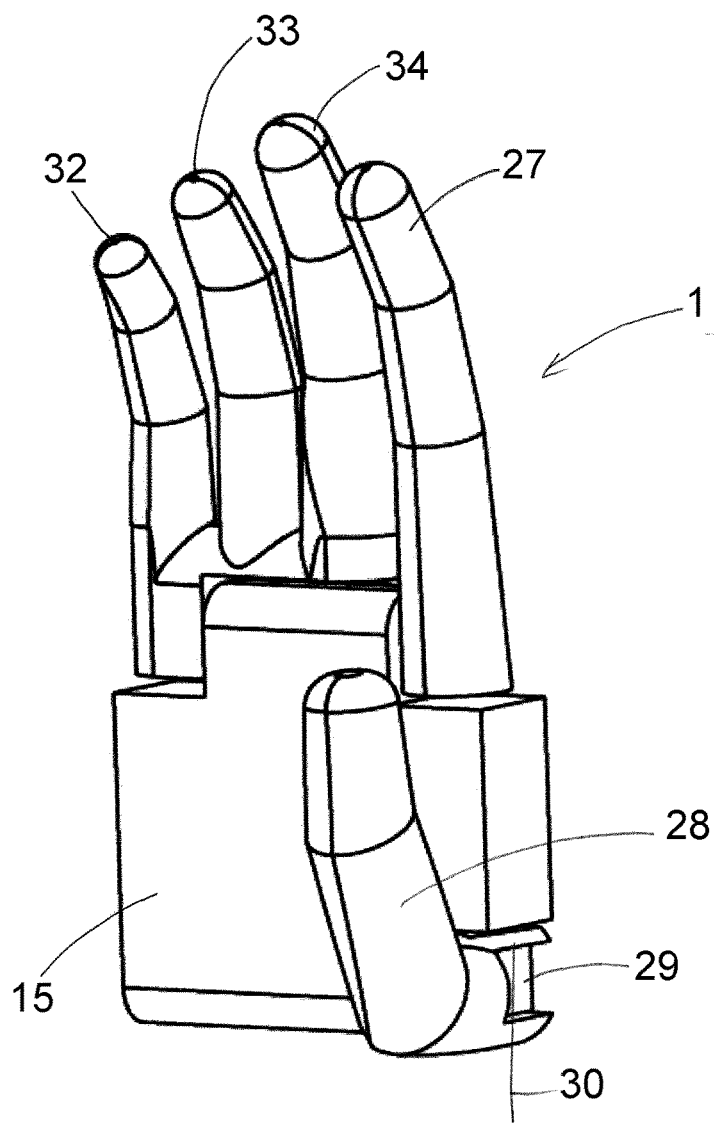
FIG. 4 the hand prosthesis as is FIG. 1 in an assembled condition.

FIG. 4 shows a hand prosthesis 1 as in FIG. 1 in a three-dimensional presentation. Hereby the third finger element 28 is rotated in the direction of the upper side 15 of the main element 3 around the rotational axis 30 of the joint 29.

In this shown embodiment, the finger elements 33, 34 are positioned above the distal side 7 of the main element 3 so that these are, in the elongated condition, positioned between the finger element 32 and the finger element 27.

Figure 5:
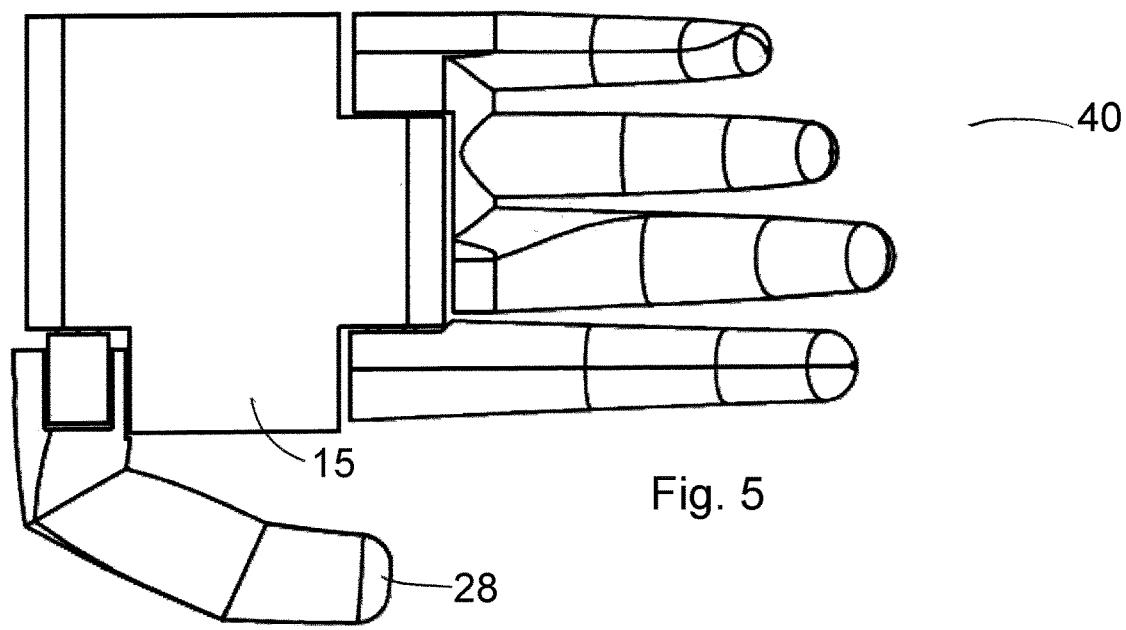
FIG. 5 the prosthesis as in FIG. 1 in a different grip function.

FIG. 5 shows a hand prosthesis 1 as in FIG. 1, wherein the finger element 28 is rotated away from the upper side 15 of the man element 3, so that the finger element 28 can more or less rest in the main plane 40 of the main element 3.

Figure 6:
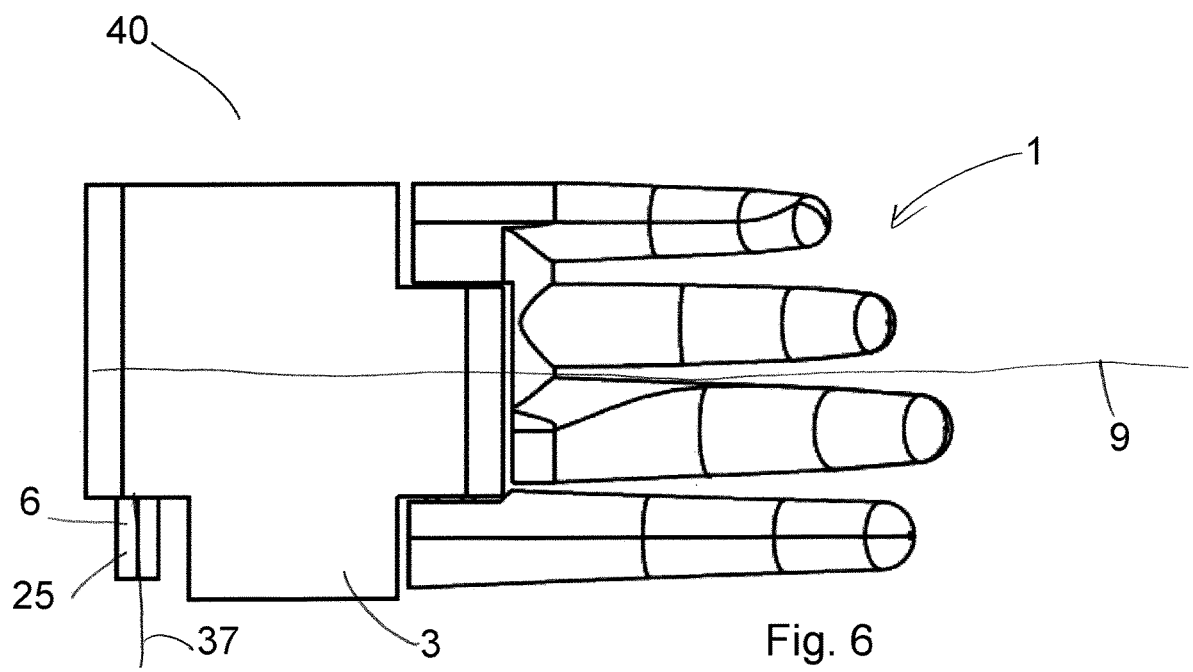
FIG. 6 the prosthesis as in FIG. 1 with a removed thumb element.

FIG. 6 shows a hand prosthesis 1 as in FIG. 1, wherein the finger element 28 is not mounted. The mounting area 25 of the coupling element 6 can be seen. The mounting area 25 has herein a non-circular, in particular a hexagonal cross-section. The rotational axis 37 of the coupling element 6 is positioned in the main plane 40 (here the character plane) of the main element 3 and positioned perpendicular to the main axis 9 of the main element 3.

Figure 7:
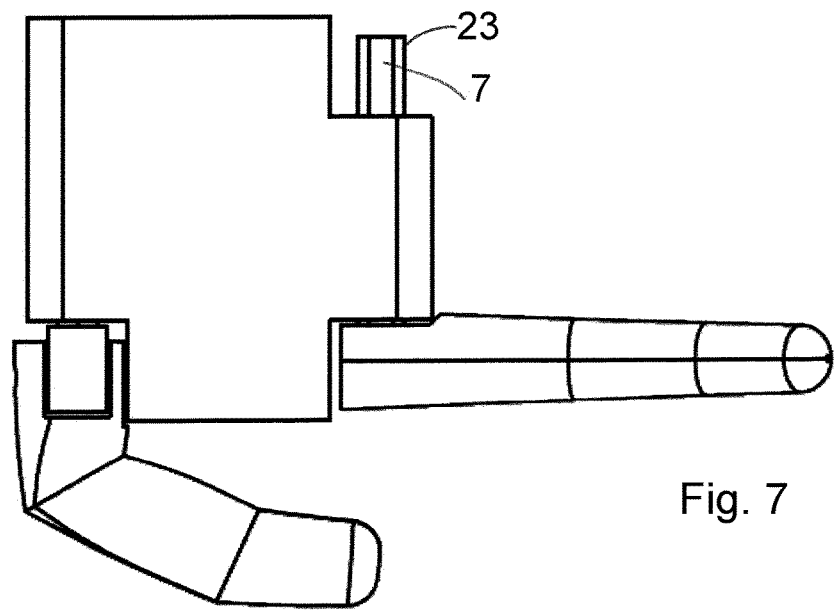
FIG. 7 the prosthesis as in FIG. 1 with a removed first finger element.
Figure 8:
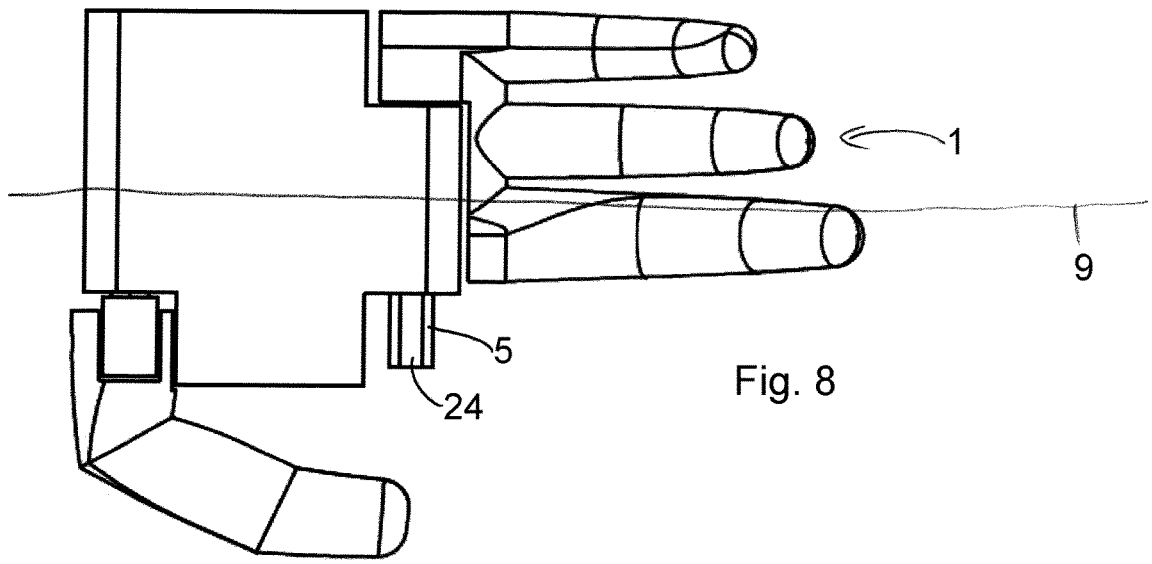
FIG. 8 the prosthesis as is FIG. 1 with a removed second finger element, FIG. 9 the prosthesis as is FIG. 1 with suggested coupling elements, FIG. 10 a hand prosthesis in transparency with a drive motor, FIG. 11 the hand prosthesis as in FIG. 10 with indicated axes of rotation, FIG. 12 the hand prosthesis as in FIG. 10 without wrist prosthesis, FIG. 13 the hand prosthesis as in FIG. 10 with indicated axes of rotation, FIG. 14 a hand prosthesis base body, FIG. 15 the hand prosthesis base body of FIG. 14 with indicated axes of rotation, FIG. 16 the hand prosthesis as in FIG. 10 in a different perspective, FIG. 17 a hand prosthesis with two drive motors, FIG. 18 the hand prosthesis as in FIG. 17 with indicated axes of rotation, FIG. 19 the hand prosthesis as in FIG. 17 in an enlargement, FIG. 20 the hand prosthesis as in FIG. 17 with indicated axes of rotation, FIG. 21 a hand prosthesis base body with two drive motors, FIG. 22 the hand prosthesis base body as in FIG. 21 with indicated axes of rotation, FIG. 23 the hand prosthesis as in FIG. 17 in an additional perspective, FIG. 24 the hand prosthesis in transparency with three drive motors, FIG. 25 the hand prosthesis as in FIG. 24 with indicated axes of rotation, FIG. 26 the hand prosthesis as in FIG. 24 in an enlargement, FIG. 27 the hand prosthesis as in FIG. 24 with plotted rotational axis's FIG. 28 a hand prosthesis base body with three drive motors, FIG. 29 a hand prosthesis base body as in FIG. 28, FIG. 30 the hand prosthesis as in FIG. 24 and in a different perspective, FIG. 31 the hand prosthesis in a tweezer grip, shown from the top, FIG. 32 the hand prosthesis as in FIG. 31 from the side, FIG. 33 the hand prosthesis as in FIG. 31 from the front, FIG. 34 the hand prosthesis executing a three-point grip, from the front, FIG. 35 the hand prosthesis in another grip position, FIG. 36 the hand prosthesis as in FIG. 35, from the top, FIG. 37 a hand prosthesis which executes a lateral grip, from the side, FIG. 38 the hand prosthesis in a different grip position, FIG. 39 the hand prosthesis as in FIG. 37, from the top, FIG. 40 the hand prosthesis as in FIG. 37, from the front, FIG. 41 the hand prosthesis executing the index finger or the stretched pointer finger, FIG. 42 a hand prosthesis in an additional grip function, FIG. 43 a hand prosthesis executing the hook grip.

FIG. 7 shows the hand prosthesis 1 as in FIG. 1, whereby the finger element 26 has been removed and the coupling element 4 can be seen. Hereby, the mounting area 24 of the coupling element 5 sticks out, perpendicular to the main axis 9 of the main element 3, from the main element 3.

Figure 9:
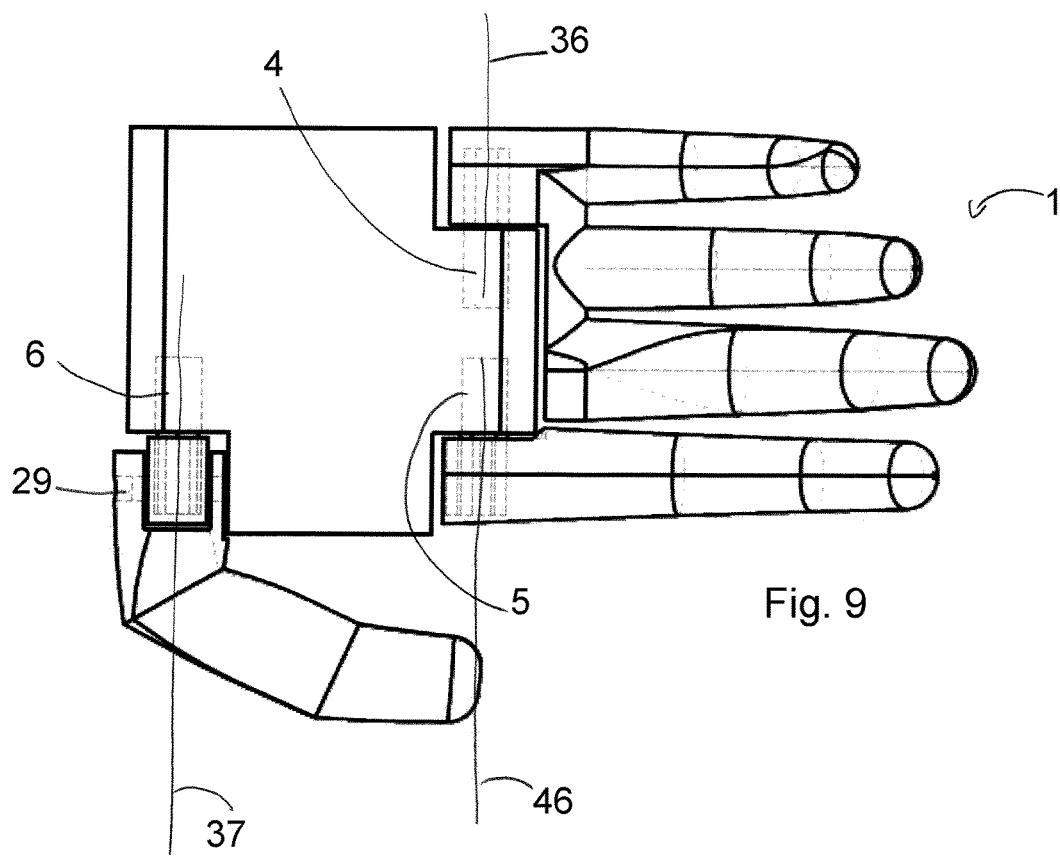

FIG. 9 shows the hand prosthesis 1 in accordance with FIG. 1, wherein the position of the coupling elements 4, 5, 6 and the joint 29 is shown. Herein, the rotational axis 36 of the coupling element 4 is nearly on the same plane as the rotational axis 46 of the coupling element 5. The rotational axis 37 of the coupling element 6 is at least almost parallel to the rotational axis 46 of the coupling element 5. Herein, the rotational axis 37 of the coupling element 6 has a proximal offset in reference to the rotational axis 46 of the coupling element 5.

Figure 10:
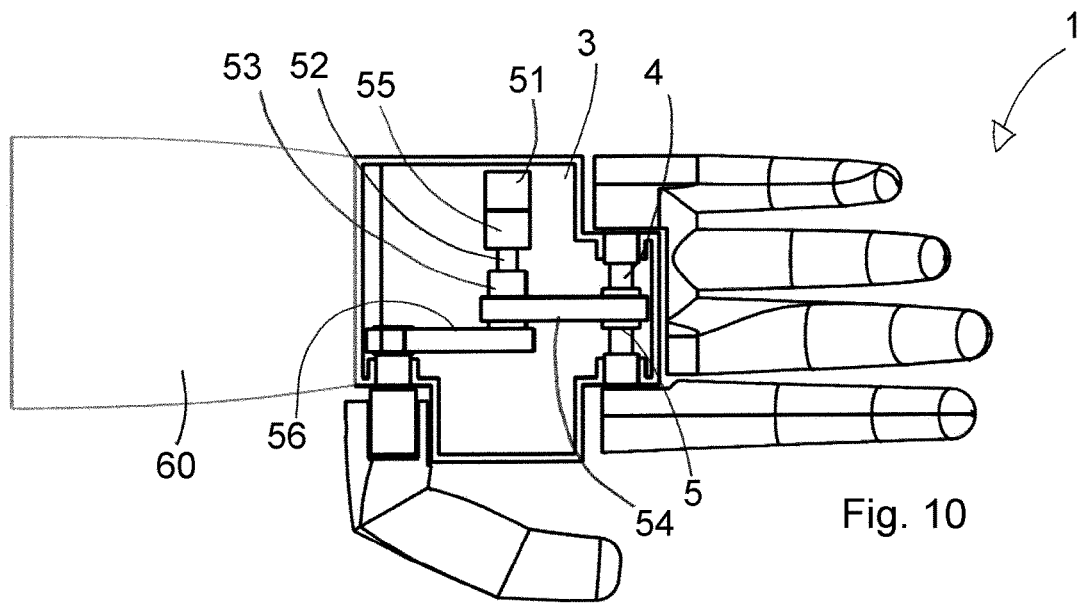

FIG. 10 shows a hand prosthesis 1, in particular a hand prosthesis 1 as it is shown in FIG. 1. Hereby, the hand prosthesis 1 comprises a motor 55, like an electric motor, in particular a servo motor, which is powered by an energy source, such as a battery and/or an accumulator. The driveshaft 52 of the motor 55 is connected with a gearing 53, which converts the rotation of the output shaft 52 into a slower rotation. Coupled to the gearing 53 is a first rotation transfer 54 through which the rotation of the output shaft of the gearing 53 is transferred to the coupling elements 4, 5. The coupling elements 4, 5 are designed as one-piece or can be coupled to each other in a rotationally fixed manner. The coupling elements 4, 5 can also be designed as separate elements and be individually connected with the rotation transfer 54 for the transfer of the rotation of the output shaft of the gearing 53 to the coupling elements 4, 5.

The coupling element 6 is, by means of the rotation transfer 56, connected with the output shaft of the gearing 53 for the transfer of the rotation of the output shaft of the gearing 53 to the coupling element 6.

The rotation transfers 54, 56 can have one or several spur gears, chains, belts, worm gears, shafts for the transfer of the rotation.

An arm element 60 is positioned proximal to the main element 3. The arm element 60 can be an artificial wrist joint, a cuff or similar, through which the main element 3 can be connected with the patient, in particular with the arm of the patient.

Figure 11:
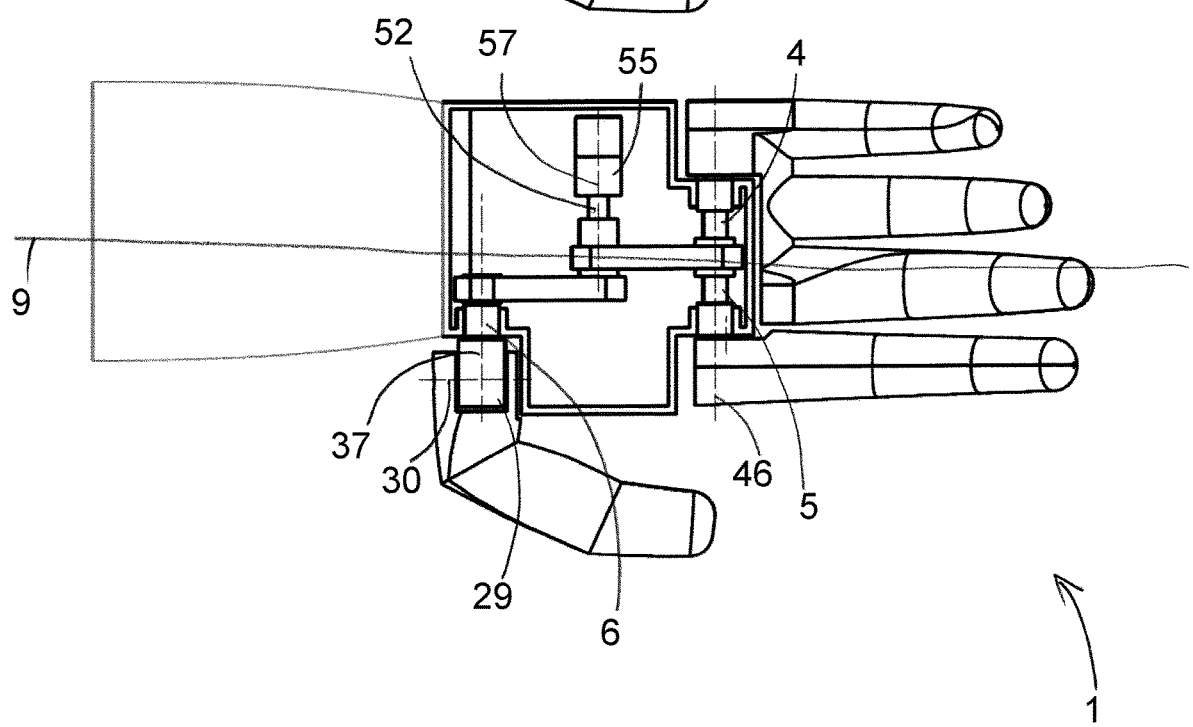

FIG. 11 shows the hand prosthesis as in FIG. 10 with the rotational axes 30, 37, 46, 57 indicated. Herein, the rotational axis 37 of the coupling element 6, a rotational axis 57 of the driveshaft 52 of the motor 55 and the rotational axis 46 of the coupling elements 4, 5 are at least substantially parallel, wherein the rotational axis 46 is positioned from distal and proximal in the order of rotational axis 46, rotational axis 57, rotational axis 37. The rotational axis 46, 57, 37 are at least more or less perpendicular relative to the main axis 9 of the main element 3.

The rotational axis 30 of the joint 29 is positioned perpendicular to the rotational axis 37.

Figure 12:
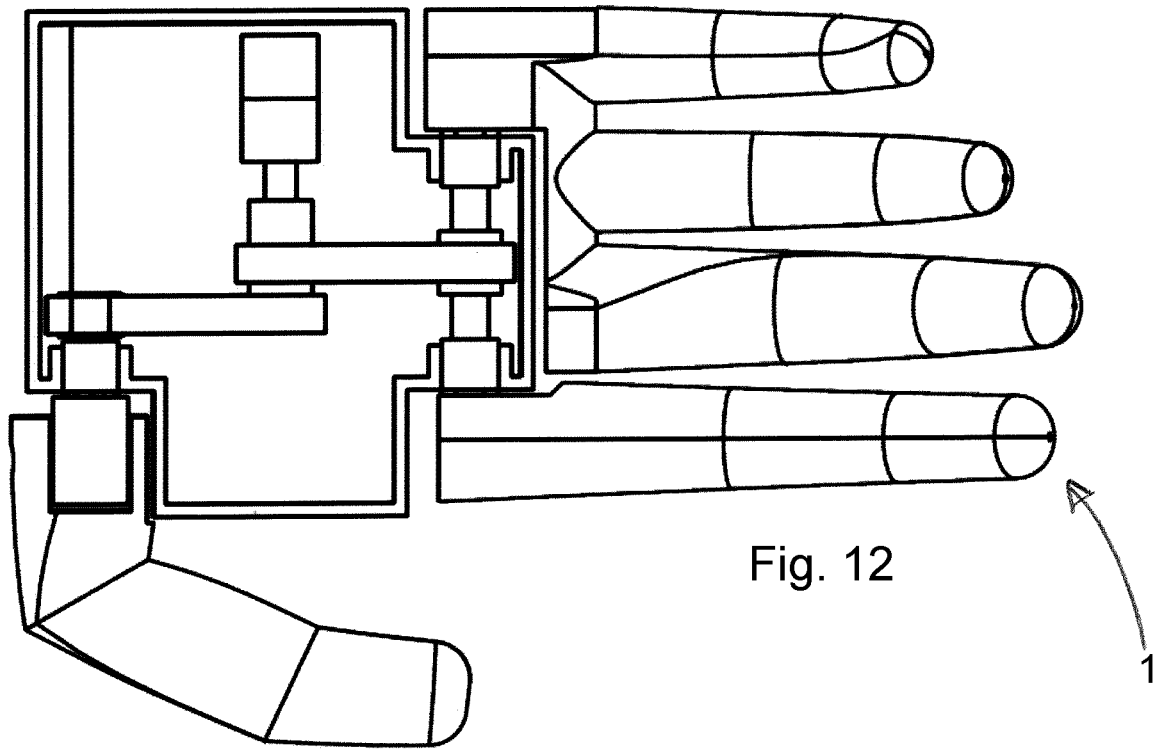

FIG. 12 shows the hand prosthesis as in FIG. 11 without the arm element 60.

Figure 13:
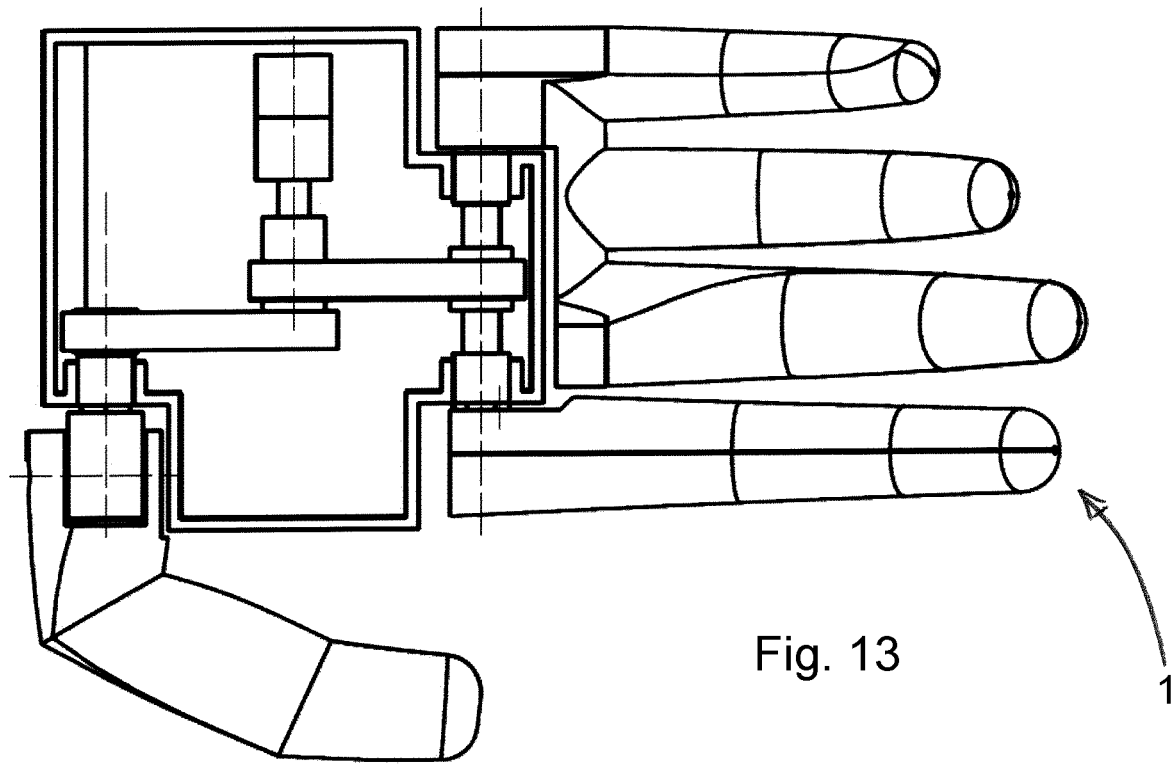

FIG. 13 shows the hand prosthesis as in FIG. 11 without the arm element 60 with the indicated rotational axes.

Figure 14:
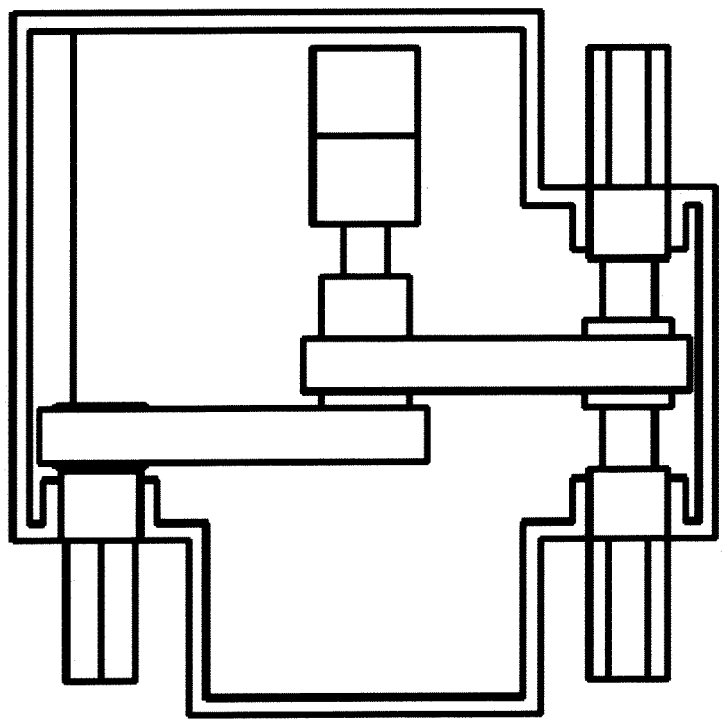

FIG. 14 shows the hand prosthesis base body 2 in accordance with FIG. 12.

Figure 15:
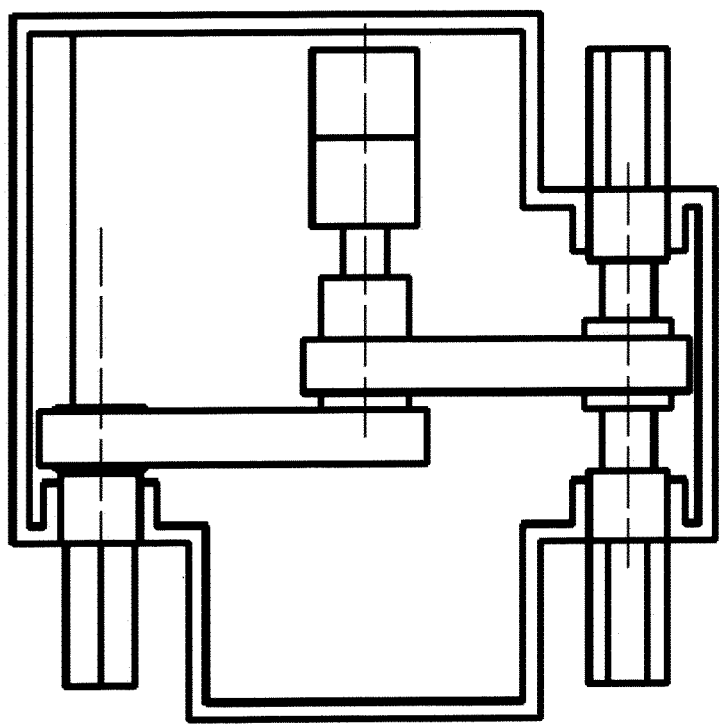

FIG. 15 shows the hand prosthesis base body 2 with the indicated rotational axes in accordance with FIG. 12

Figure 16:
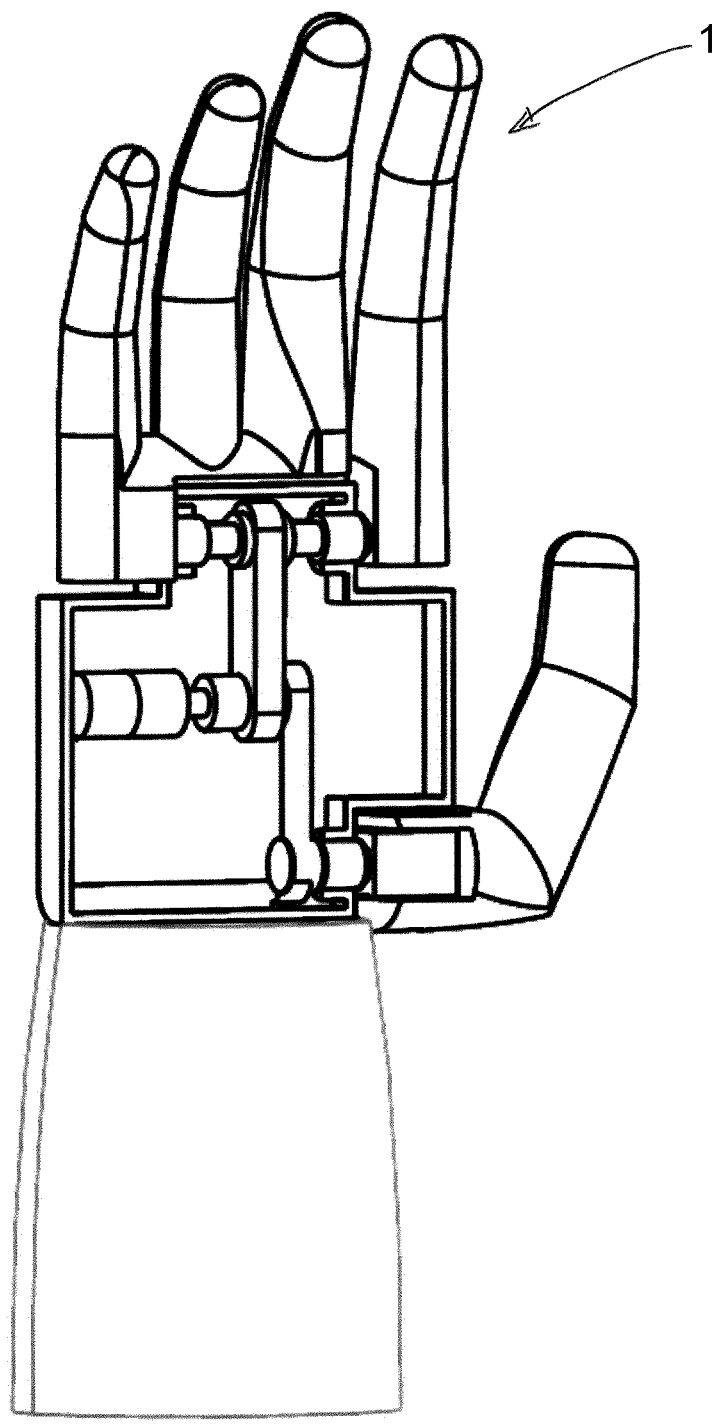

FIG. 16 shows a hand prosthesis 1 in a three-dimensional view in accordance with FIG. 12.

Figure 17:
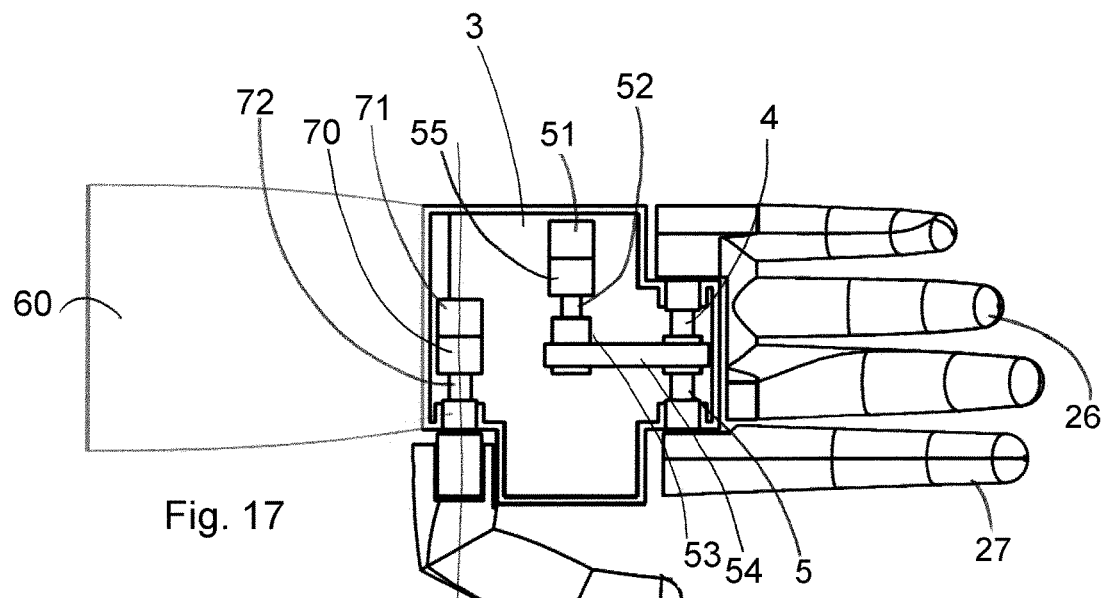

FIG. 17 shows a hand prosthesis 1 in a sectional view. The outer part of the hand prosthesis 1 can be designed in accordance with FIG. 1. The hand prosthesis 1 has a first motor 55, in particular an electro motor, to drive the finger elements 26, 27. The motor 55 is powered by the energy source 51. The output shaft 52 of the motor 55 is connected with the gearing 53 which lowers the rotational speed of the output shaft 52. The rotation transfer 54 is connected with the output shaft of the gearing 53, which transfers the rotation of the output shaft of the gearing 53 to the coupling elements 4, 5. The rotation transfer 54 can also, in addition to the gearing 53 or instead of the gearing 53, decrease or increase the rotation of the output shaft of the gearing 53 or the output shaft 52 of the motor.

A second motor 70 is positioned in the inner part of the main element 3 to process the rotational movement of the finger element 28 around the rotational axis 37. The second motor 70 is a equipped with the energy supply 71, in particular a battery or an accumulator. The output shaft 72 of the second motor 70 can be connected with gearing, which provides the gear reduction for the rotation movement of the output shaft 72 and transfers it to the coupling element 6.

Figure 18:
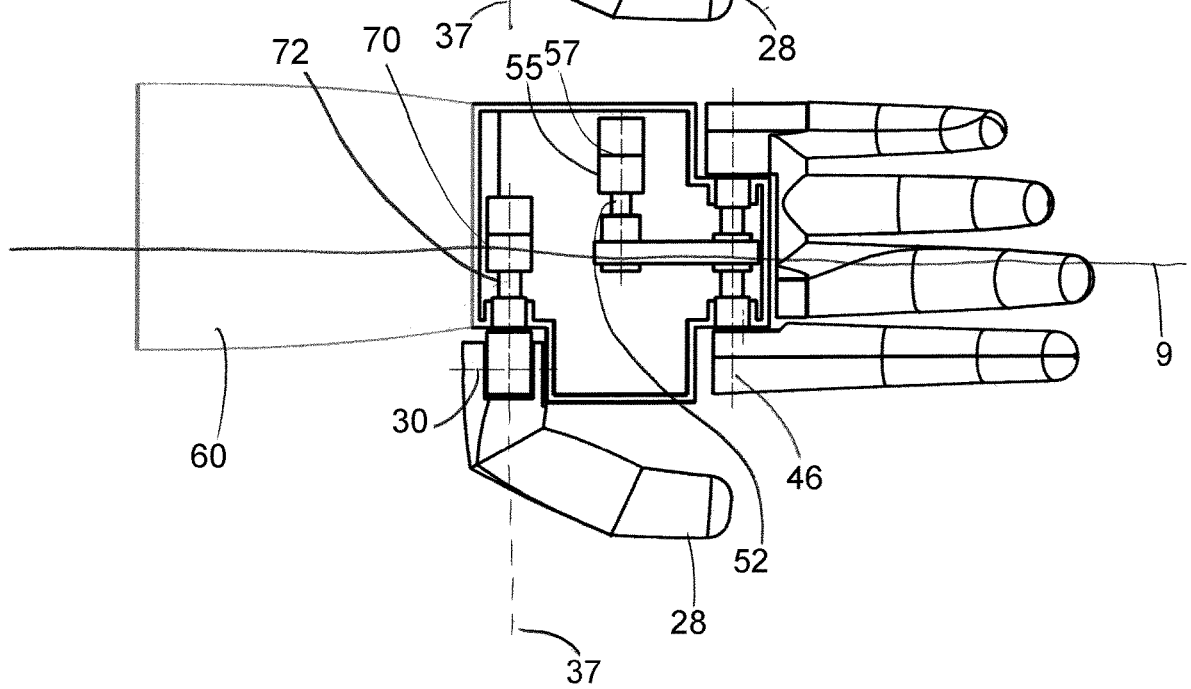

FIG. 18 shows a rotational axis 46 around which the finger elements 26 and 27 rotate, the rotational axis 57 around which the output shaft 52 of the first motor 55 rotates, and the rotational axis 37, around which the finger element 28 rotates, and the output shaft 72 of the second motor 70 rotates. The three rotational axes 37, 46, 57 are at least substantially parallel and arranged from distal and proximal in the order of 46, 52, 37. The three rotational axes 37, 46, 57 are positioned perpendicular to the main axis 9 of the main element 3.

The second rotational axis 30 of the finger element 28 is positioned perpendicular relative to the rotational axis 37.

Figure 19:
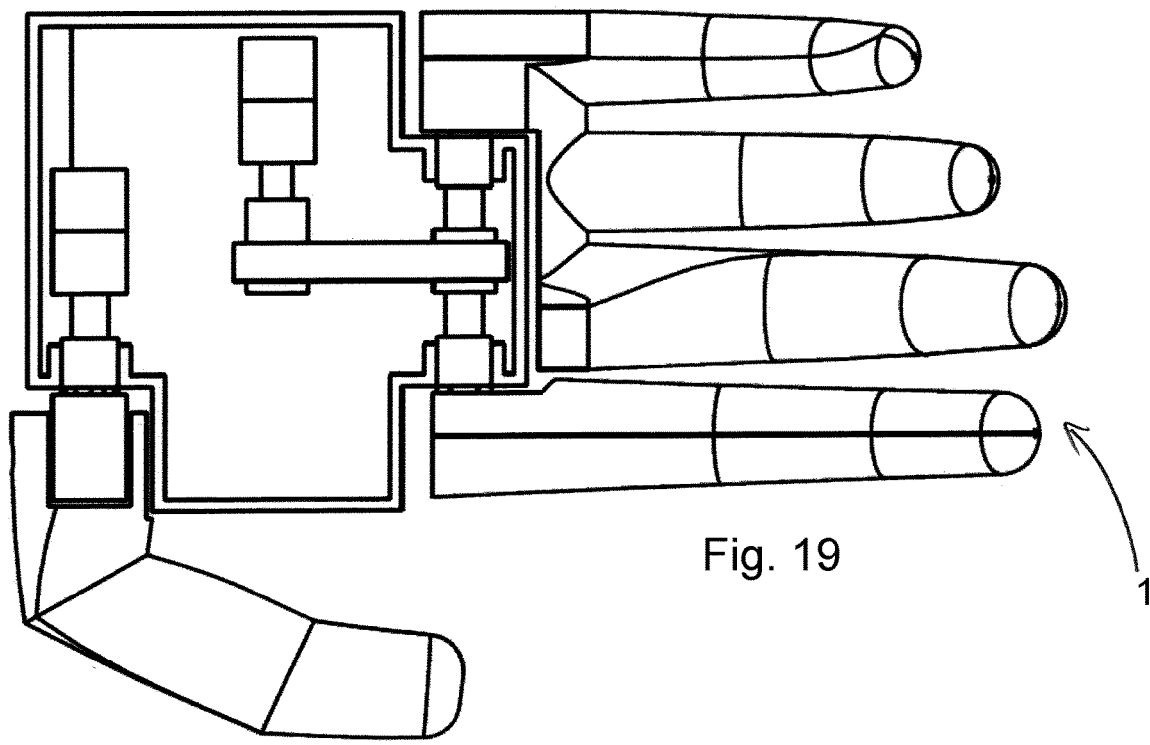
Figure 20:
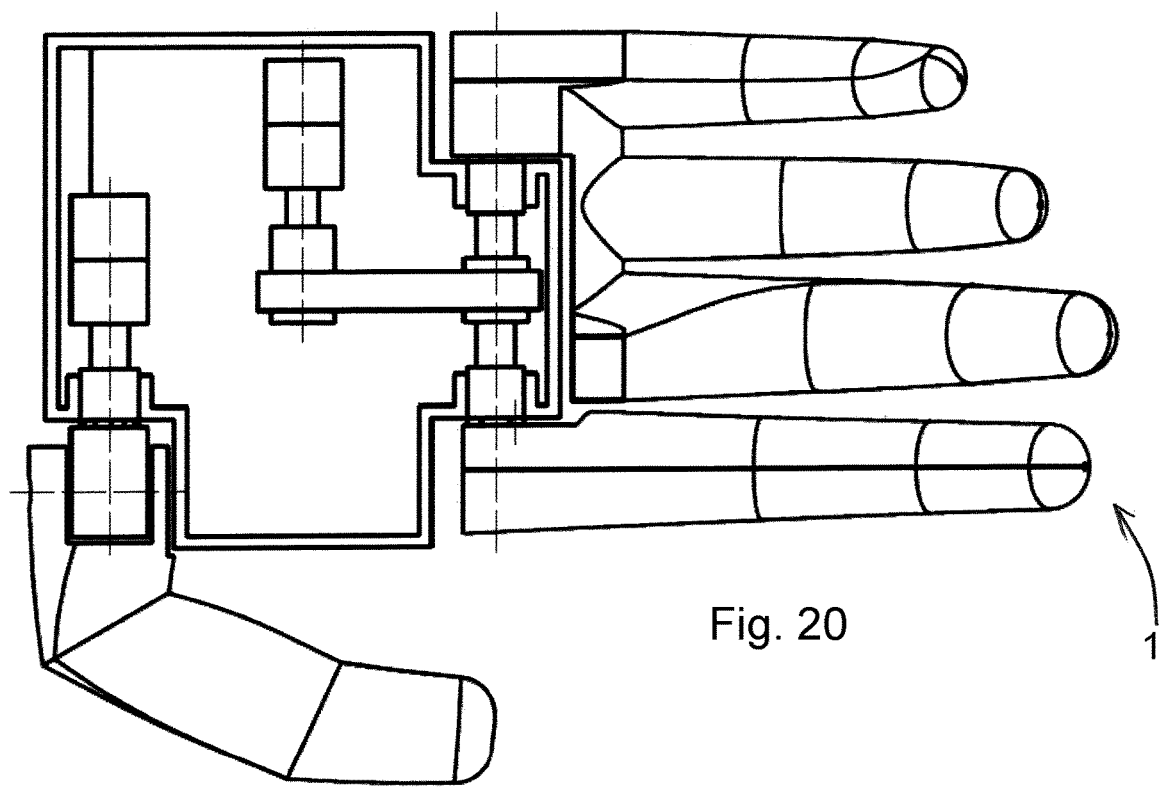

FIG. 19 and FIG. 20 show the hand prosthesis 1 as in FIG. 17 enlarged and without arm element 60.

Figure 21:
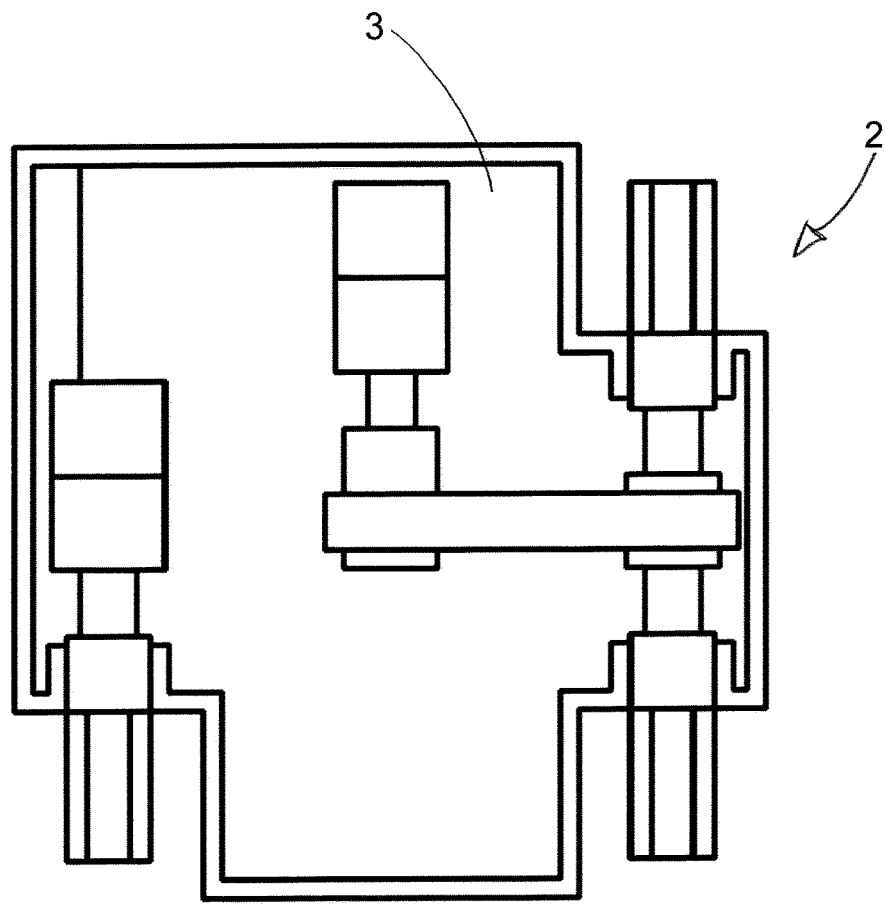
Figure 22:
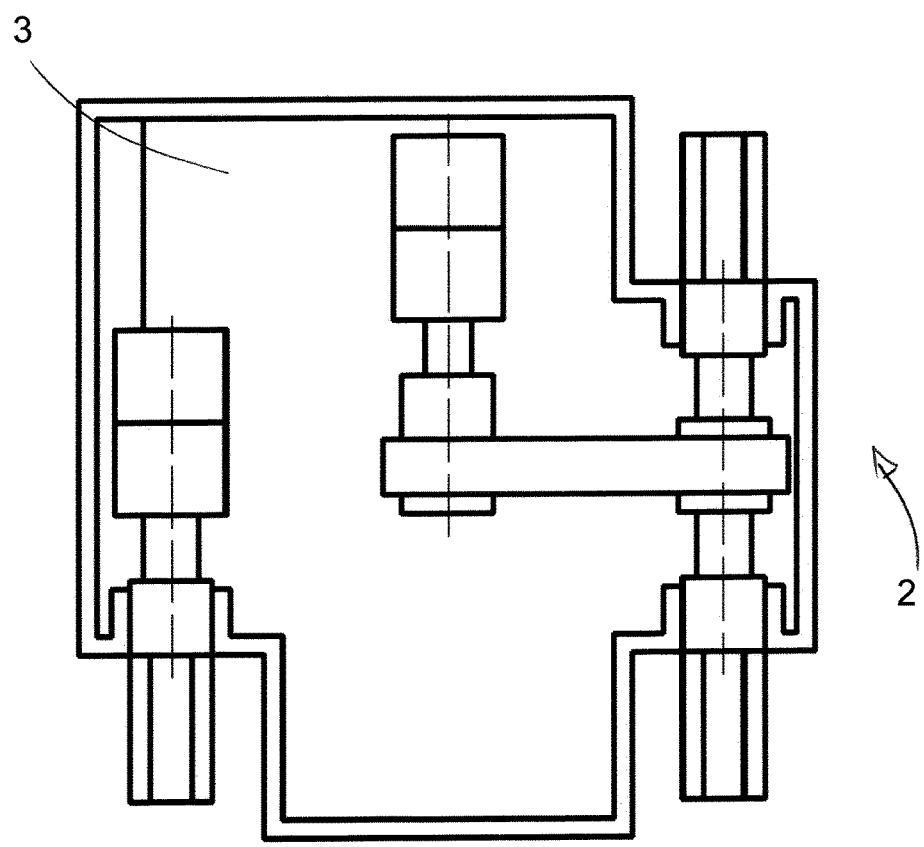

FIG. 21 and FIG. 22 show the hand prosthesis base body 2 in accordance with FIG. 18 with the main element 3.

Figure 23:
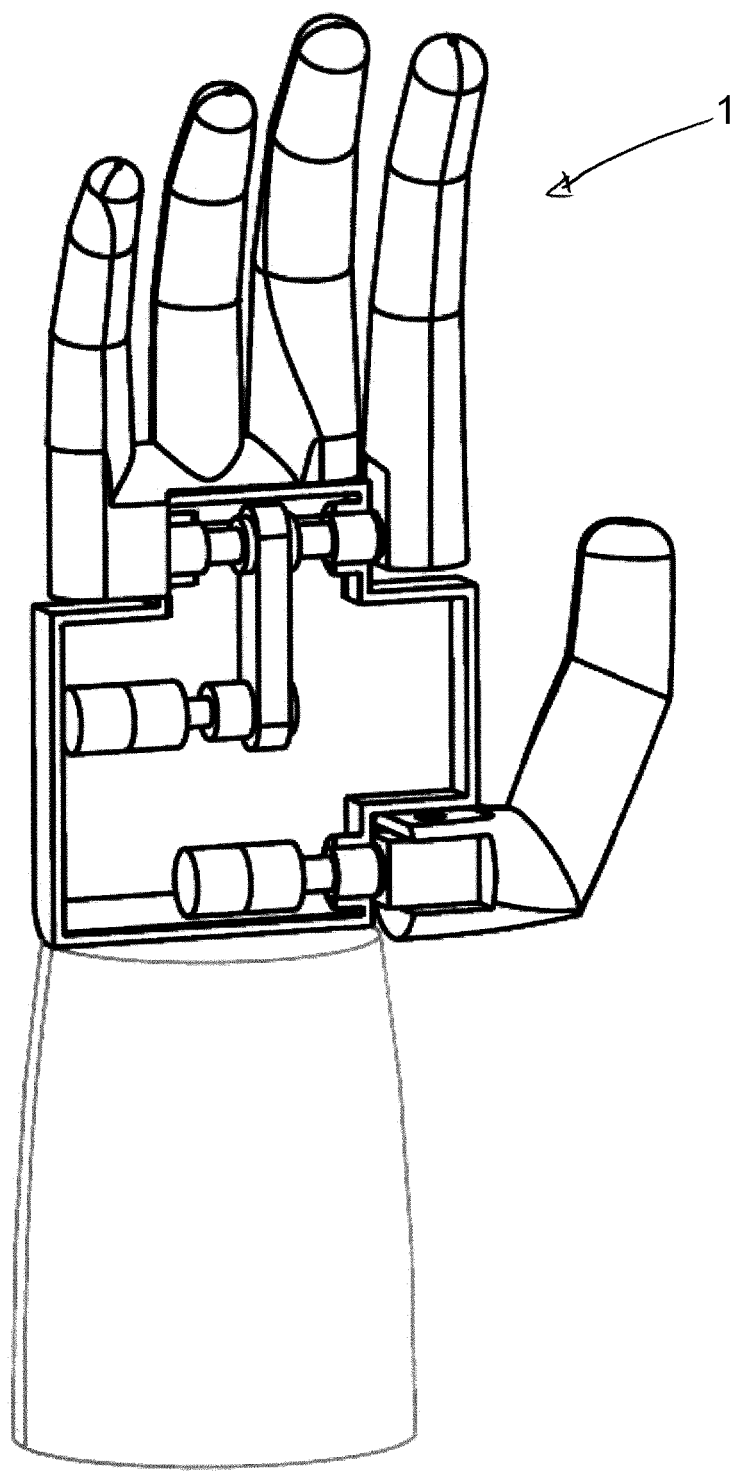

FIG. 23 shows the hand prosthesis 1 in accordance with FIG. 17 in a three-dimensional view.

Figures 24, 25:
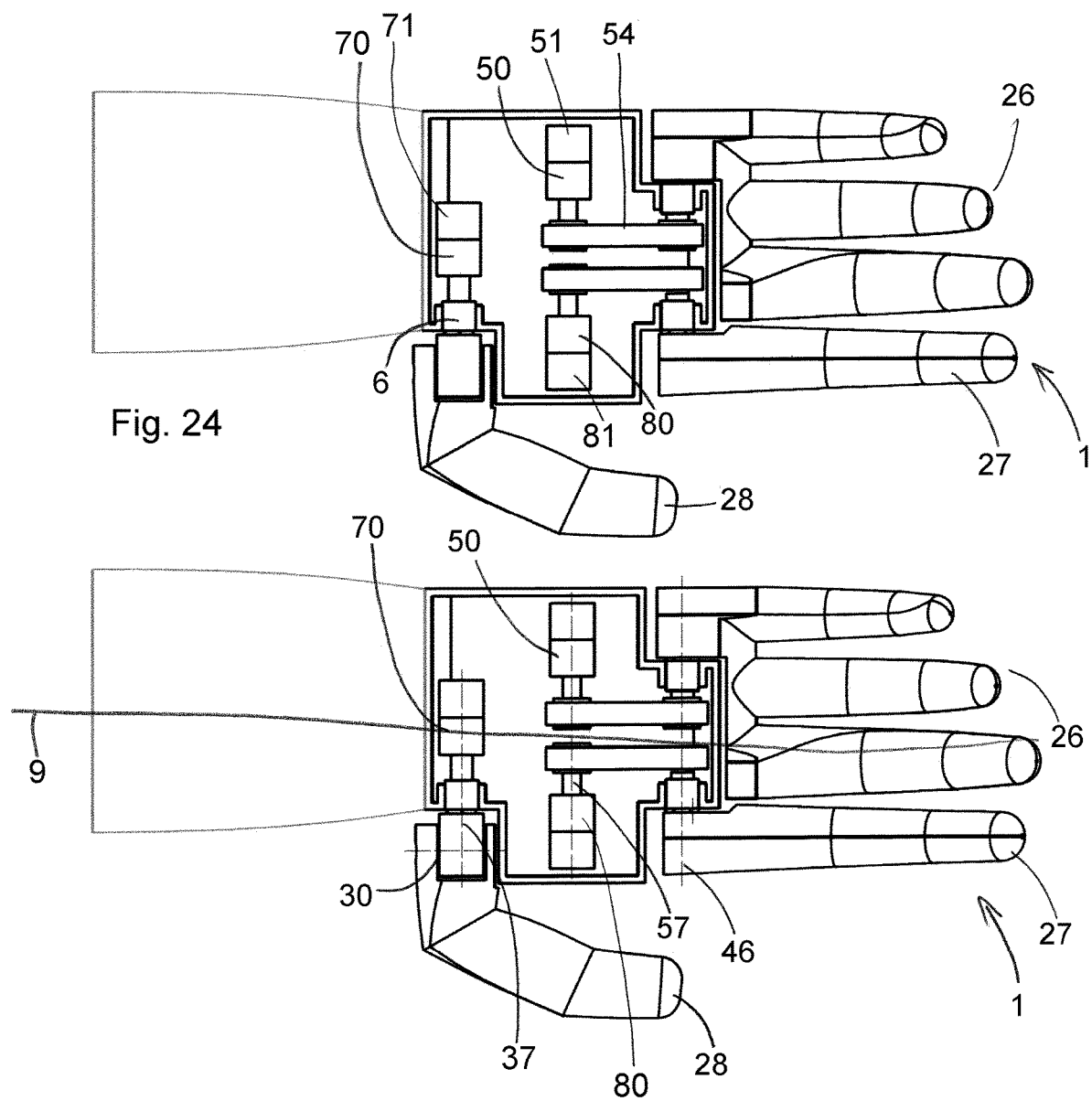

FIG. 24 shows an additional embodiment of the hand prosthesis 1, wherein the finger elements 26, 27, 28 can be moved relative to each other independently. The hand prosthesis 1 has at least three motors 50, 70, 80 which are supplied with energy by the respective energy sources 51, 71, 81. The motors 50, 70, 80 can hereby be electro motors, such as for instance servo motors. The output shaft of the motor 50 is possibly connected through gearing with the rotation transfer 54. The rotation transfer 54 transfers the rotational movement of the output shaft of the motor 50 to the coupling element 4. Through the rotational movement of the coupling element 4, the finger element 26 is pivoted.

The output shaft of the motor 70 can be connected in a rotationally fixed manner with the coupling element 6. Through the rotational movement of the coupling element 6, the finger element 28 is pivoted.

The output shaft of the motor 80 can be connected by gearing with a rotation transfer 56'. The rotation transfer 56' transfers the rotational movement of the output shaft of the motor 80 to the coupling element 5. Through the rotational movement of the coupling element 5, the finger element 27 is pivoted.

FIG. 25 shows a hand prosthesis 1 of the embodiment in accordance with FIG. 24 with indicated rotational axes 30, 37, 46, 57. The finger element 26 can be rotated around the rotational axis 46, the finger element 27 can also be rotated around the rotational axis 46. The rotational axis 46 is perpendicular to the main axis 9 of the hand prosthesis 1. The output shaft of the motor 55 and the output shaft of the motor 80 rotate around the rotational axis 57 which is at least substantially parallel to the rotational axis 46. The output shaft of the motor 70 rotates around the rotational axis normal 37, around which the finger element 28 can pivot. The finger element 28 can also pivot around the rotational axis 30 which is perpendicular relative to the rotational axis 37. The rotational axis 57 is positioned between the rotational axis 46 and 37.

Figure 26:
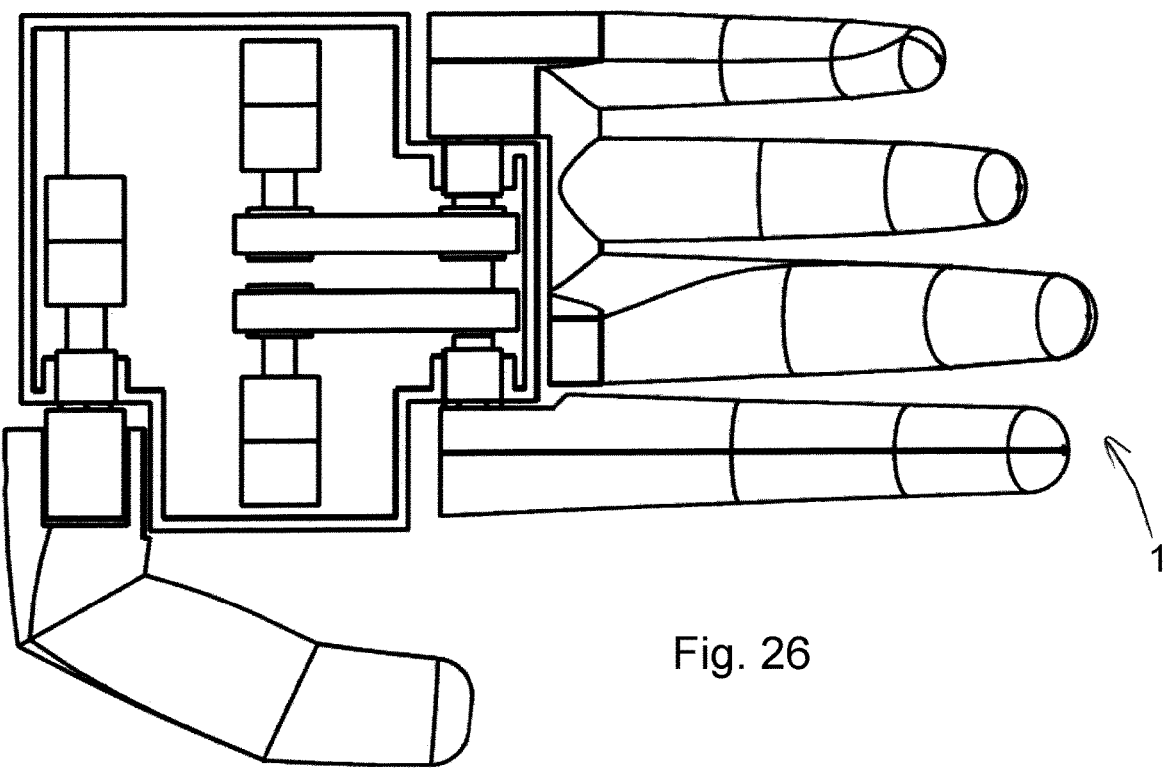
Figure 27:
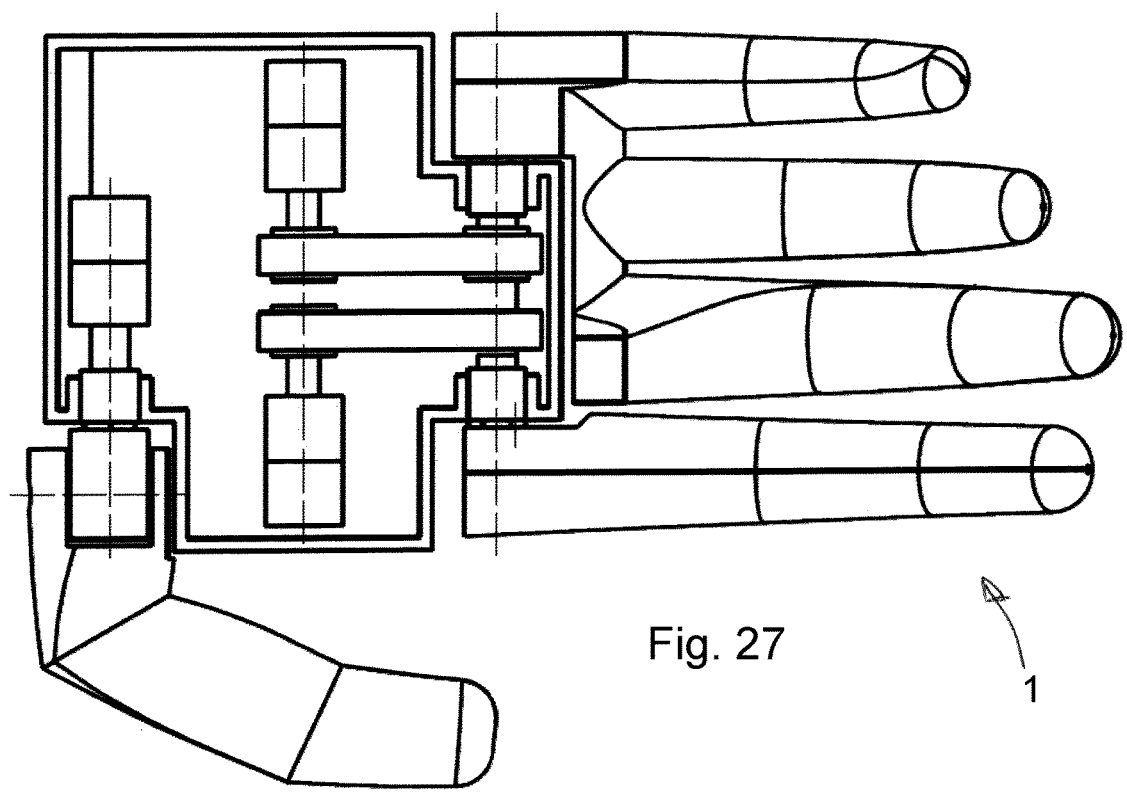

FIG. 26 and FIG. 27 show the hand prosthesis 1 in accordance with the embodiment in FIG. 24 without arm element 60 in the enlargement.

Figure 28:
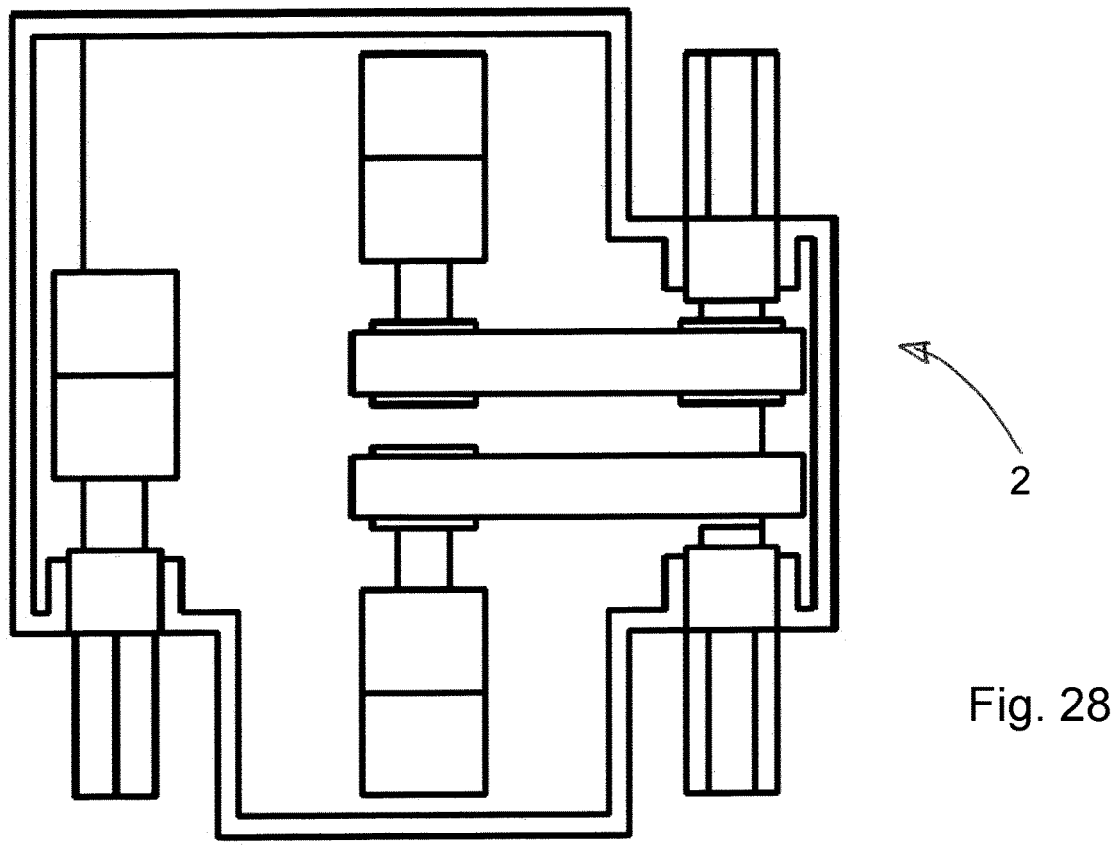
Figure 29:
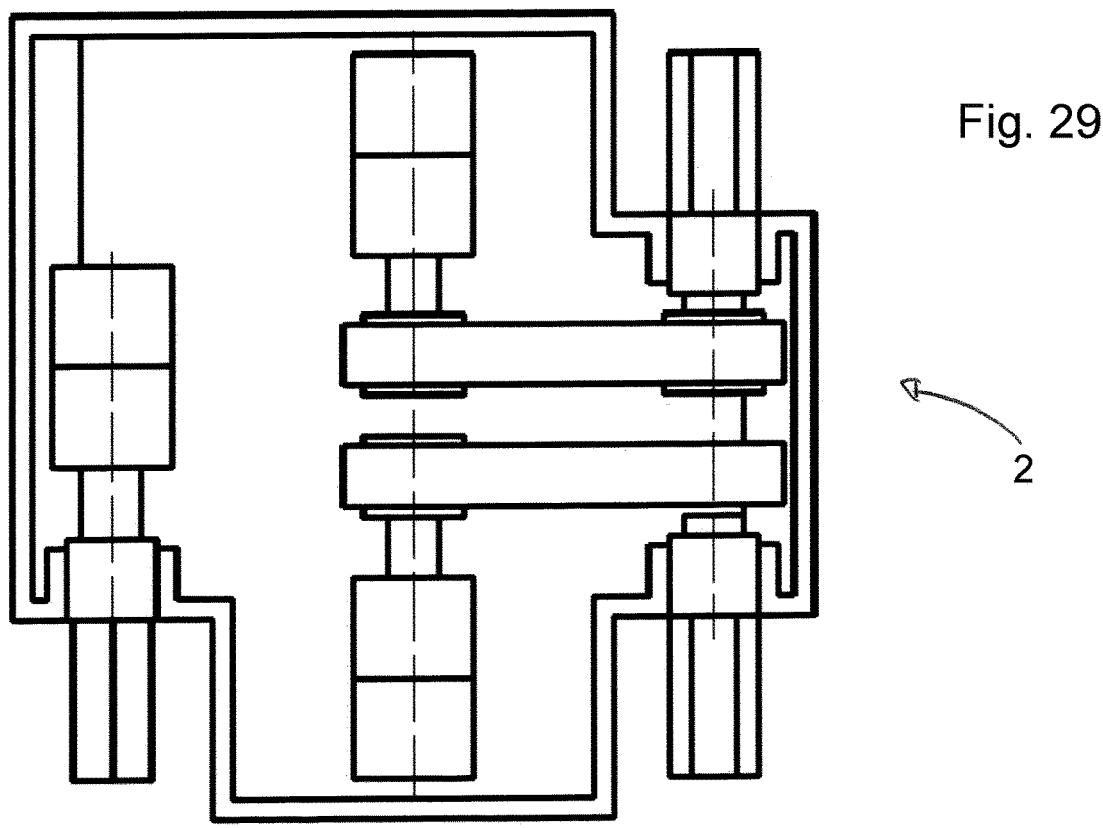

FIG. 28 and FIG. 29 show the hand prosthesis base body 2 in accordance with the embodiment in FIG. 24.

Figure 30:
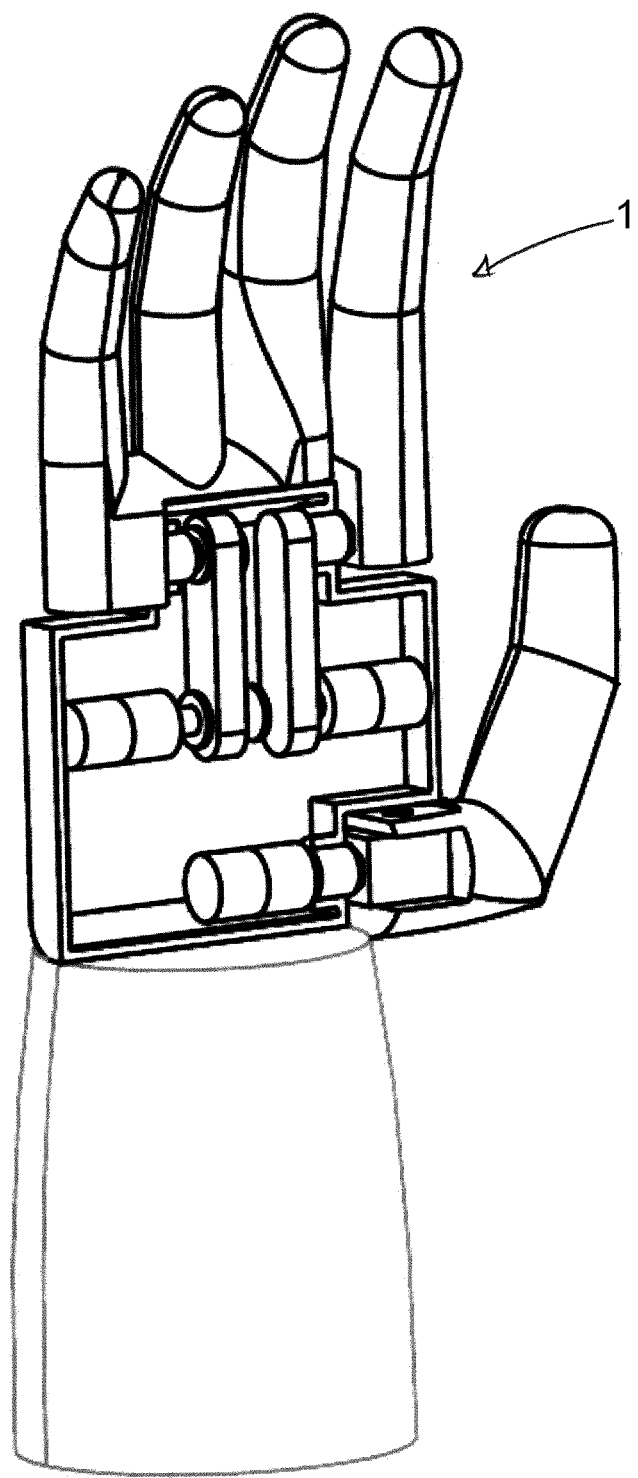

FIG. 30 shows the hand prosthesis 1 in particular in the embodiment of FIG. 24 in a perspective view.

Figure 31:
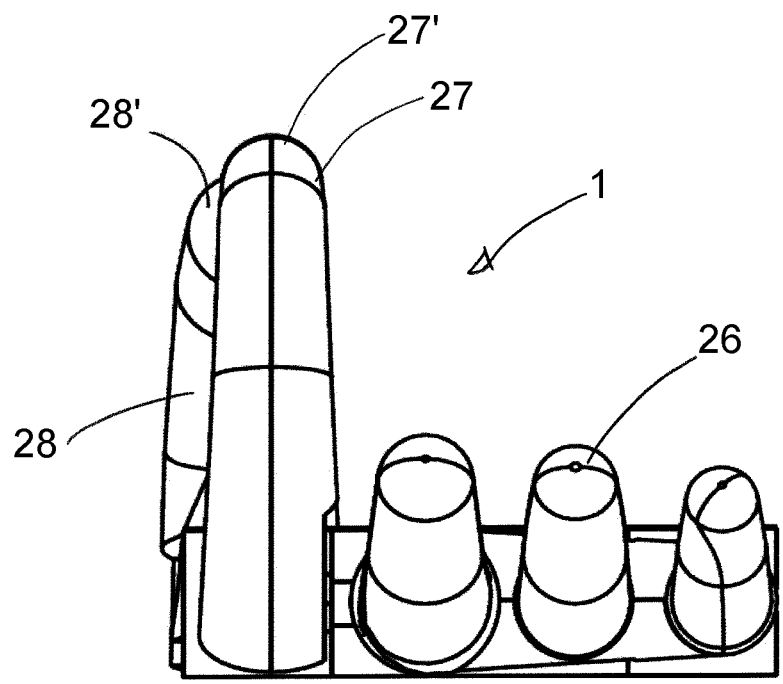

FIG. 31 shows the hand prosthesis 1, in particular according to the embodiment of FIG. 24 from distal. The finger element 26 is herein stretched and is nearly positioned in the plane of the hand prosthesis base body 2. The finger element 27 is bent in the proximal direction, the tip 27' of the finger element 27 touches the tip 28' of the finger element 28.

Thus, the finger element 28 sticks out from the main plane of the hand prosthesis base body 2.

Figure 32:
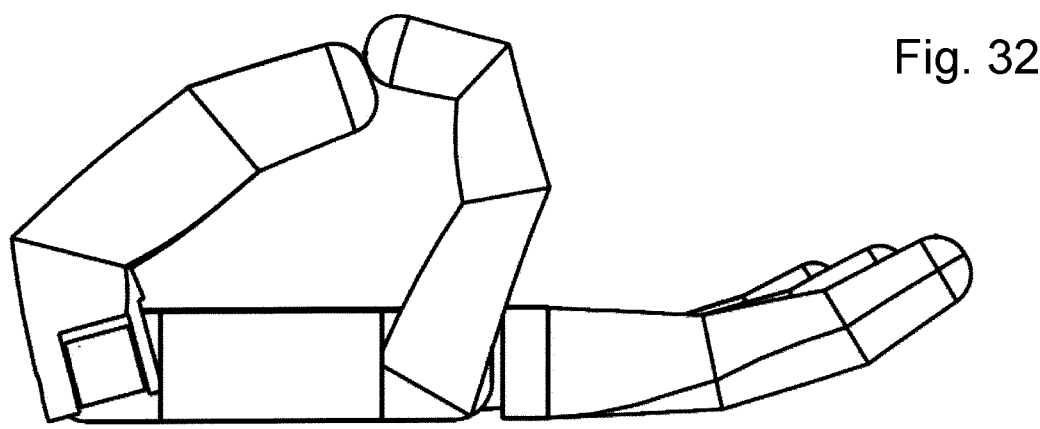
Figure 33:
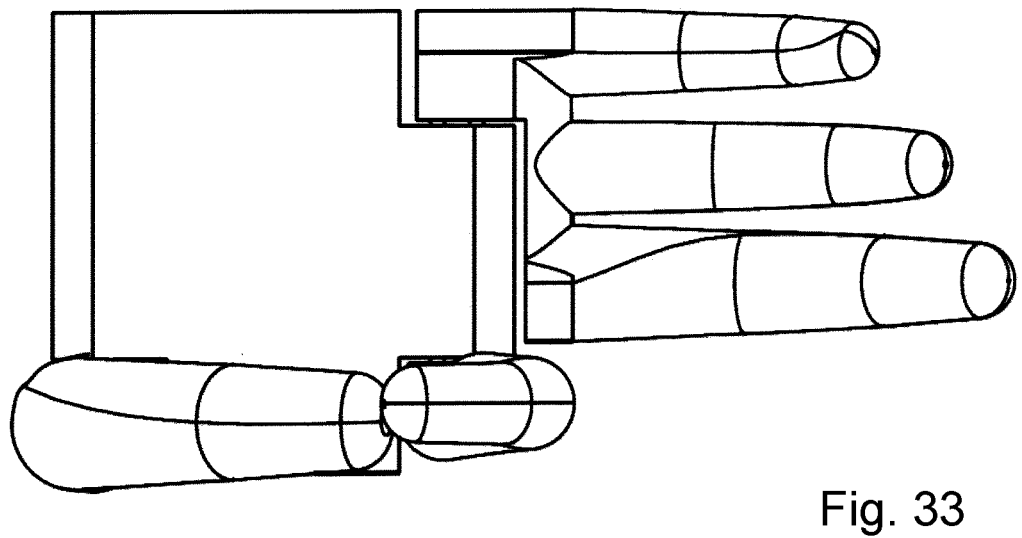

FIG. 32 and FIG. 33 show the grip position from the side and from the inner part of the hand.

Figure 34:
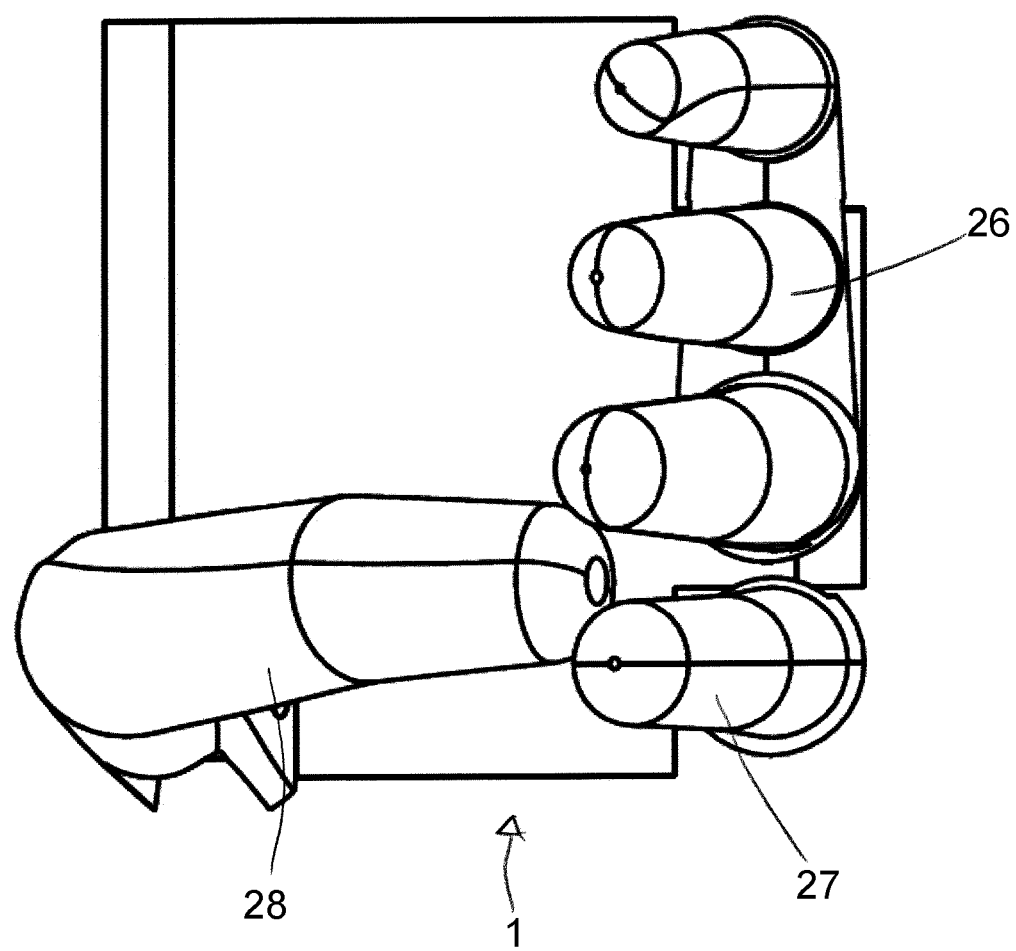

FIG. 34 shows an additional grip position of the hand prosthesis 1, wherein the finger elements 27 and 28 are positioned in accordance with FIG. 31, and the finger element 26 is also pivoted in the proximal direction. Thus, the finger elements 26 in 27 can be positioned next to each other.

Figure 35:
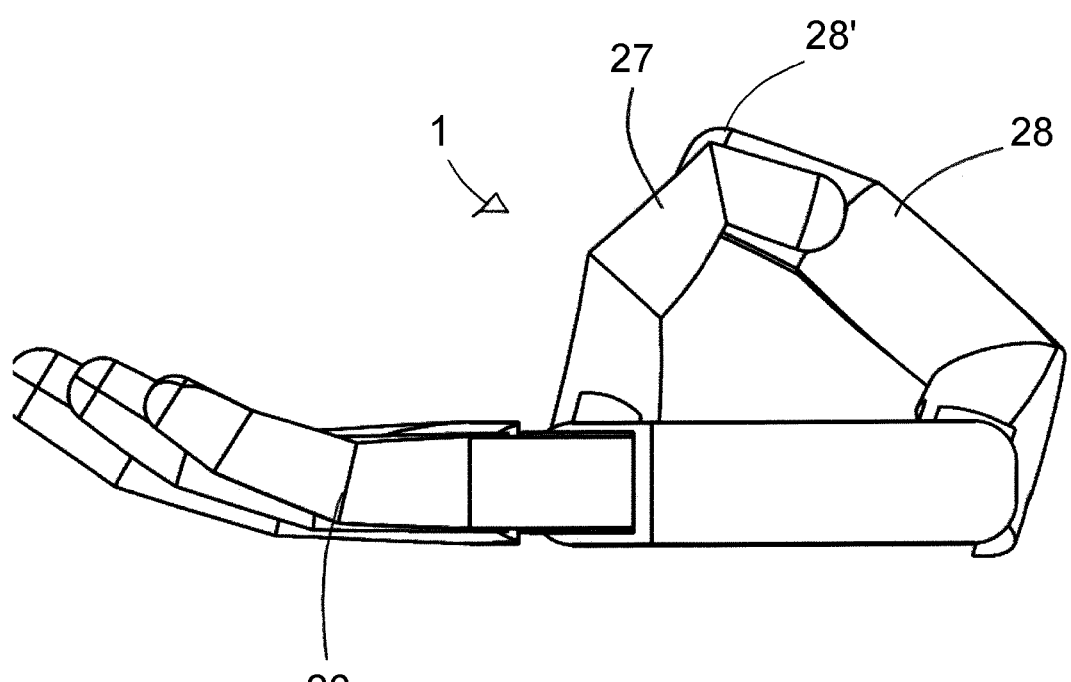

FIG. 35 shows a third grip position of the hand prosthesis 1, wherein the finger element 26 is stretched, the finger element 27 in the direction of the inner hand surface, meaning in the proximal direction, and the finger element 28 is also stretched in the direction of the inner hand surface, however, pivoted around the rotational axis 30 in a way such that the tip 28' of the finger element 28 is positioned at the side of the finger element 28 which faces away from the finger element 26.

Figure 36:
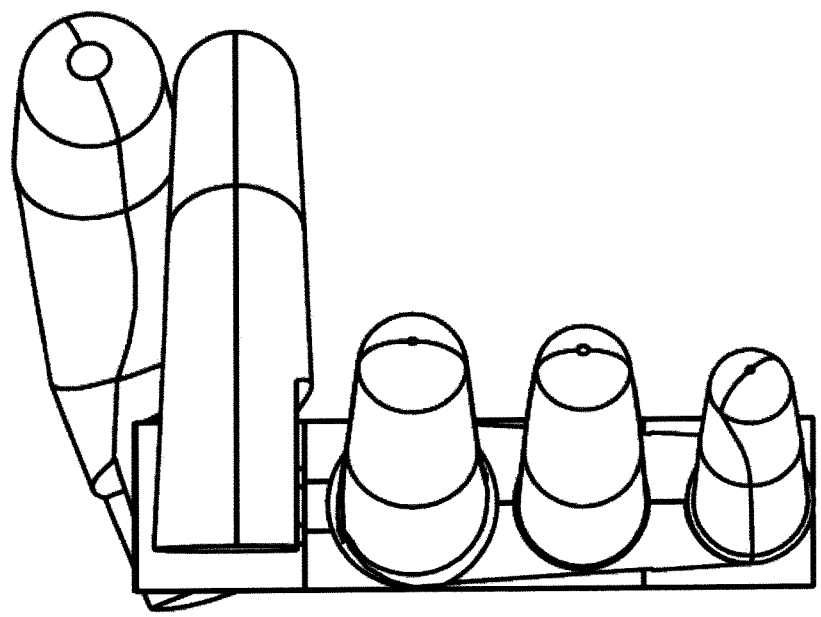

FIG. 36 shows the grip positioned as in FIG. 35 from distal.

Figure 38:
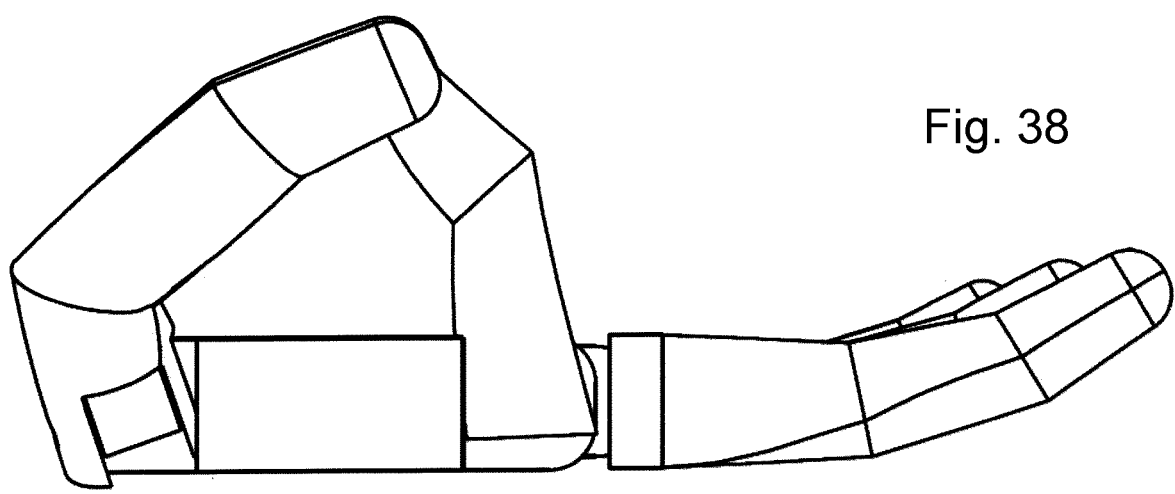

FIG. 38 shows the third grip position from the side.

Figure 37:
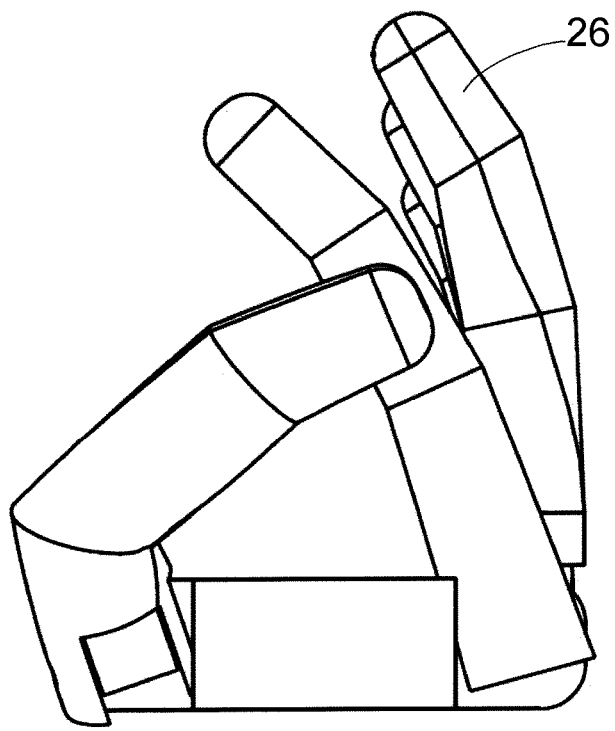

FIG. 37 shows a fourth grip position which differs from the third grip position in a way that the finger element 26 is also pivoted in the proximal direction.

Figure 39:
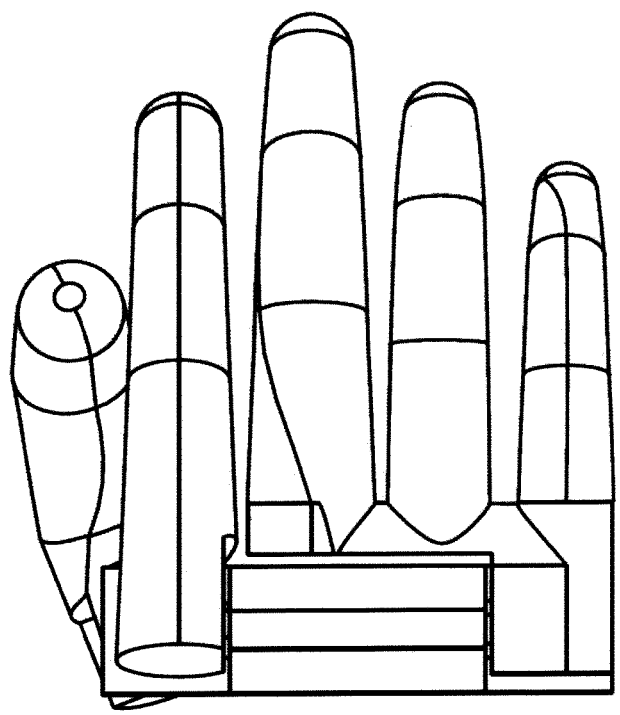

FIG. 39 shows the fourth grip position from distal.

Figure 40:
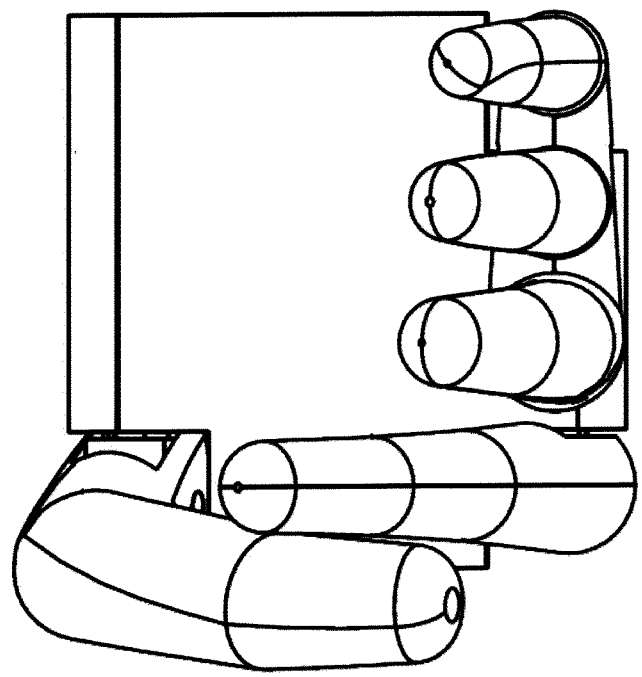

FIG. 40 shows the fourth grip position from above.

Figure 41:
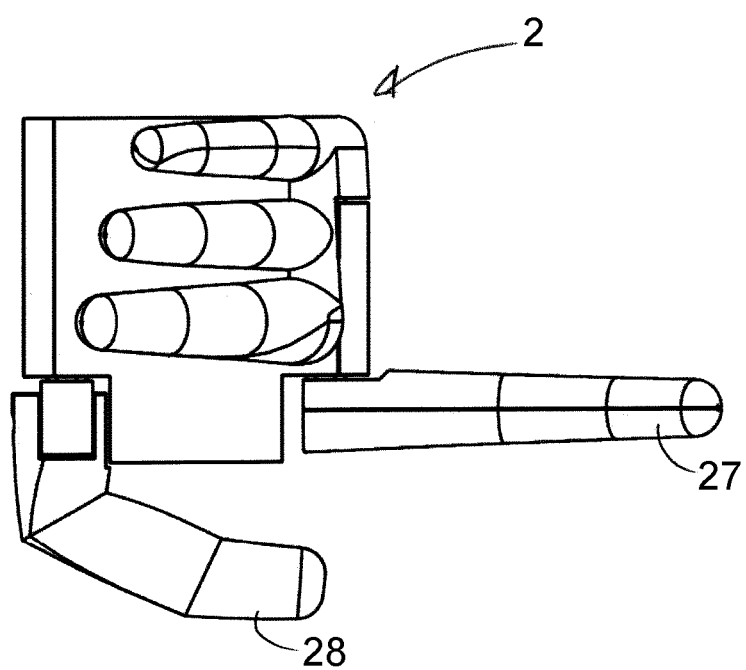

FIG. 41 shows a fifth grip position, wherein the finger element 28 is positioned in the main axis of the hand prosthesis base body 2. The finger element 27 is stretched in the distal direction and is also positioned in the main plane of the hand prosthesis base body 2. The finger element 26 is bent in the proximal direction.

Figure 42:
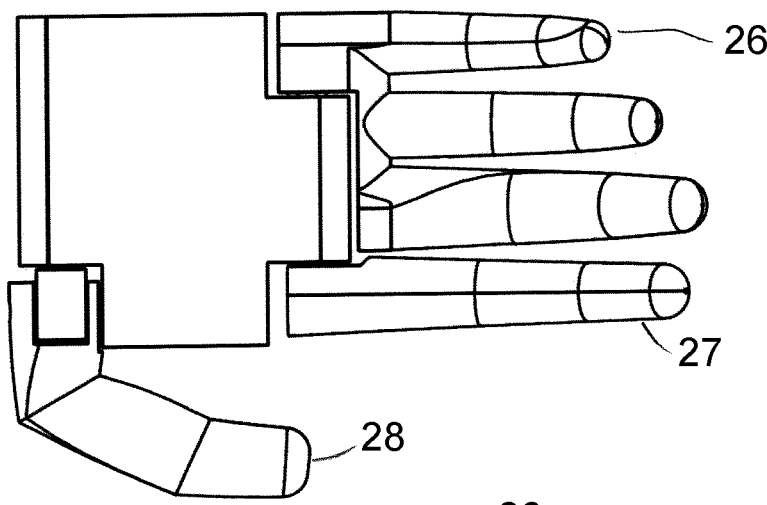

FIG. 42 shows a sixth grip position whereby all three finger elements 26, 27, 28 are stretched.

Figure 43:
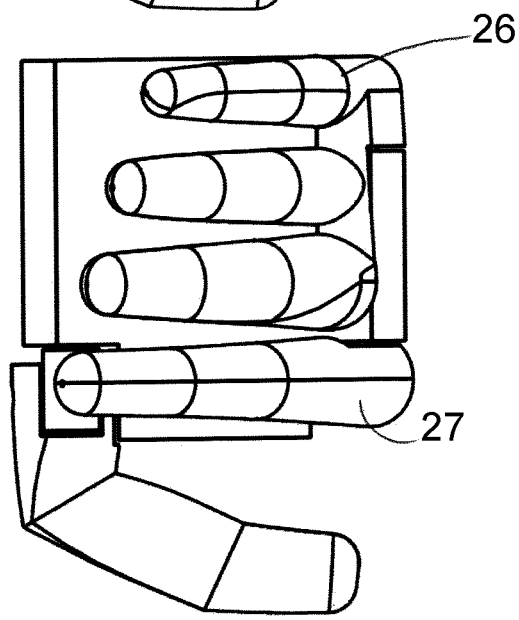

FIG. 43 shows a seventh grip position, whereby the finger elements 26 and 27 are bent in the proximal direction and the finger element 28 is positioned in the main plane of the hand prosthesis base body 2.

REFERENCE CHARACTERS

1 Hand Prosthesis
2 Hand Prosthesis Base Body
3 Main Element
4 First Coupling Element
5 Second Coupling Element
6 Third coupling element
7 Distal side of the main element
8 Proximal side of the main element
9 Main axis of the main element
10 First recess
11 Second recess
12 Third recess
13 First side of the main element
14 Second side of the main element
15 Top side of the main element
16 Bottom side of the main element
17 Third side of the main element
18 Fourth side of the main element
19 Fifth side of the mail element
20 Sixth side of the main element
21 Right side of the main element
22 Left side of the main element
23 First mounting area
24 Second mounting area
25 Third mounting area
26 First finger element
27 Second finger element
28 Third finger element
29 Joint
30 Rotational axis of the joint
31 Main axis of the third coupling element
32 First finger part element
33 Second finger part element
34 Third finger part element
35 Mounting area
36 Rotational Axis
37 Main plane of the main element
38 First pin of the joint
39 Second pin of the joint
40 Main plane of the main element
41 First limb of the third finger element 28
42 Second limb of the third finger element
43 Finger section of the third finger element 28
44 Mounting area of the second finger element 27
45 Partial finger element of the second finger element 27
46 Rotational axis of the coupling element 5
47 Opening
48 Main axis of the second finger element 27
49 Opening
50 Opening
51 Energy source 52 Drive shaft
53 Gearing
54 First rotation transfer
55 Motor
56 Rotation transfer
56' Rotation transfer
57 Rotational axis
60 Arm element
70 Second motor
71 Energy source
72 Output shaft
80 Third motor

The invention claimed is:

1. A hand prosthesis base body comprising:
an outer side,
a motor having a rotatable output shaft,
a first rotatable shaft being functionally connected with the output shaft of the motor,
the first rotatable shaft having a detachable coupling element which releasably couples at least one finger element to the first rotatable shaft such that the at least one finger element is removable from the hand prosthesis base body,
a second coupling element releasably couples a second finger element to the hand prosthesis base body, and at least one of the detachable coupling element and the second coupling element is positioned at a side of the hand prosthesis base body, and
a second shaft is connected with the second coupling element, the second shaft has a rotational axis which is parallel to a rotational axis of the first rotatable shaft.

2. The hand prosthesis base body according to claim 1, wherein the detachable coupling element is designed for movement and holding of the at least one finger element.

3. The hand prosthesis base body according to claim 1, wherein a rotational axis of the first rotatable shaft is perpendicular to a main shaft of the hand prosthesis base body.

4. The hand prosthesis base body according to claim 1, wherein the detachable coupling element is positioned at a distal end of the hand prosthesis base body.

5. The hand prosthesis base body according to claim 1, wherein a rotational axis of the second coupling element is positioned parallel to a rotational axis of the detachable coupling element.

6. The hand prosthesis base body according to claim 1, wherein the detachable coupling element has a non-round cross-section for an interlocking connection of the finger element with the detachable coupling element.

7. The hand prosthesis base body according to claim 1, wherein an additional coupling element releasably couples another finger element to the hand prosthesis base body, the detachable coupling element and the additional coupling element are positioned at a distal end of the hand prosthesis base body.

8. A hand prosthesis comprising:
a hand prosthesis base body having an outer side,
a motor having a rotatable output shaft,
a first rotatable shaft being functionally connected with the output shaft of the motor,
the first rotatable shaft having a detachable coupling element which releasably couples at least one finger element to the first rotatable shaft such that the at least one finger element is detachable from the hand prosthesis base body,
at least one of the hand prosthesis base body and the finger element having an actuating mechanism which is actuatable to release the finger element from the hand prosthesis base body, and the actuating mechanism being actuatable, without tools, from outside the hand prosthesis base body,
a second coupling element releasably couples a second finger element to the hand prosthesis base body, and at least one of the detachable coupling element and the second coupling element is positioned at a side of the hand prosthesis base body, and
a second shaft is connected with the second coupling element, the second shaft has a rotational axis which is parallel to a rotational axis of the first rotatable shaft.

* * * * *